US008445455B2

(12) United States Patent
Lee

(10) Patent No.: US 8,445,455 B2
(45) Date of Patent: May 21, 2013

(54) STRESS-RESPONSIVE INDUCTION OF A THERAPEUTIC AGENT AND METHODS OF USE

(75) Inventor: Amy Lee, San Marino, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/084,772

(22) Filed: Apr. 12, 2011

(65) Prior Publication Data
US 2011/0268701 A1 Nov. 3, 2011

Related U.S. Application Data

(60) Division of application No. 10/928,806, filed on Aug. 27, 2004, now Pat. No. 7,923,243, which is a continuation of application No. 09/606,804, filed on Jun. 28, 2000, now Pat. No. 7,049,132.

(60) Provisional application No. 60/141,505, filed on Jun. 28, 1999.

(51) Int. Cl.
*A61K 31/70* (2006.01)

(52) U.S. Cl.
USPC ........................................ 514/44 R

(58) Field of Classification Search
USPC ........................................ 514/44 R
See application file for complete search history.

(56) References Cited

U.S. PATENT DOCUMENTS

| 5,196,523 A | 3/1993 | Lee |
| 5,811,231 A | 9/1998 | Farr et al. |
| 6,087,129 A | 7/2000 | Newgard et al. |

OTHER PUBLICATIONS

Anderson et al., "Human gene therapy," *Nature*, 392: 25-30, (1998).
Cao et al., "Requirement of Tyrosine- and Serine/Threonine Kinases in the Transcriptional Activation of the Mammalian grp78/Bi) Promoter by Thapsigargin," *J. Biol. Chem.*, 270(1): 494-502 (1995).
Chang et al., "Rat gene encoding the 78-kDA glucose-regulated protein GRP78: Its regulatory sequences and ehe efrect of protein glycosylation on its expression," *Proc. Natl. Acad. Sci. USA*, 84:680-684 (1980).
Gazit et al., "Use of the Stress-Inducible grp78/BiP Promoter in Targeting High Level Gene Expression in Fibrosarcoma in Vivo," *Cancer Res.*, 55:1660-1663 (1995).
Gazit et al., "Use of the Glucose Starvation-inducible Glucose-regulated Protein 78 Promoter in Suicide Gene Therapy of Murine Fibrosarcoma," *Cancer Res.*, 59: 3100-3106 (1999).
Gomez-Navarro et al., "Gene Therapy for Cancer," *Eur. J. Cancer*, 35:868 (1999).
Kyu Seong Kim et al., "Expression of the Glucose-Regulated Proteins (GRP94 an GRP78) in Differentiated and Undifferentiated Mouse Embryonic Cells and the Use of the GRP78 promoter as an expression system in embryonic cells" Differentiation, Springer Verlag, DE, vol. 42, No. 3, Feb. 1990 pp. 153-159.
Li et al., "Transactivation of the grp78 Promoter by $Ca^{2+}$ Depletion," *J. Biol. Chem.*, 268(16):12003-12009 (1993).
Little et al., "Generation of a Mammalian Cell Line Deficient in Glucose-regulated Protein Stress Induction through Targeted Ribozyme Driven by a Stress-inducible Promoter," *J. Biol. Chem.*, 270(16): 9526-9534 (1995).
Little et al., "The glucose-regulated proteins (GRP78 and GRP94): function, gene regulation, and applications," *Critical Rev. Euk. Gene Exp.*, 4(1):1-18 (1994).
Mullen, "Metabolic Suicide Genes in Gene Therapy," *Pharmac. Ther.*, 63:199-207 (1994).
Roy B et al., "The Mammalian Endoplasmic Retriculum Stress Response Element Consists of an Evolutionarily conserved tripartite structure and interacts with a novel stress-inducible complex," *Nucl. Acids Res.*, 27(6):1437-1443 (1999).
Roy et al., "Transduction of Calcium Stress through Interaction of the Human Transcription Factor CBF with the Proximal CCAAT Regulatory Element of the grp 78/BiP Promoter," *Mol. Cell. Biol.*, 15(4):2263-2274 (1995).
Tillman et al., "Structure and regulation of the mouse GRP78 (BiP) promoter by glucose and calcium ionophore," *Gene*, 158(2):225-229 (1995).
Verma et al., "Gene therapy—promises, problems and prospects," *Nature*, 389:239-242 (1997).
Vile et al., "Cancer gene therapy: hard lessons and new courses," *Gene Ther.*, 7:2-8 (2000).
Walther et al., "Targeted vectors for gene therapy of cancer and retroviral infections," *Mol. Biotechnol.*, 6:267-286 (1996).
Yang and Sarnow, "Location of the internal ribosome entry site in the 5' non-coding region of the immunoglobulin heavy-chain binding protein (BiP) mRNA: evidence for specific RNA-protein interactions," *Nucl. Acids Res.*, 25(14):2800-2807 (1997).
Yoshida H et al., "Identification of the CIS-Acting Endoplasmic Reticulum Stress Response Element Responsible for Transcriptional Induction of Mammalian Glucose-Regulated Proteins" *J. Biol. Chem.*, 273(50): 33741-33749 (1998).

*Primary Examiner* — Brian Whiteman
(74) *Attorney, Agent, or Firm* — Fish & Richardson P.C.

(57) ABSTRACT

This invention relates to compositions and methods for selective expression of a heterologous nucleic acid sequence in a targeted tissue, and more particularly to the glucose regulated protein 78 (grp78) stress-responsive promoter and its use in gene therapy and the production of transgenic animals.

8 Claims, 10 Drawing Sheets
(4 of 10 Drawing Sheet(s) Filed in Color)

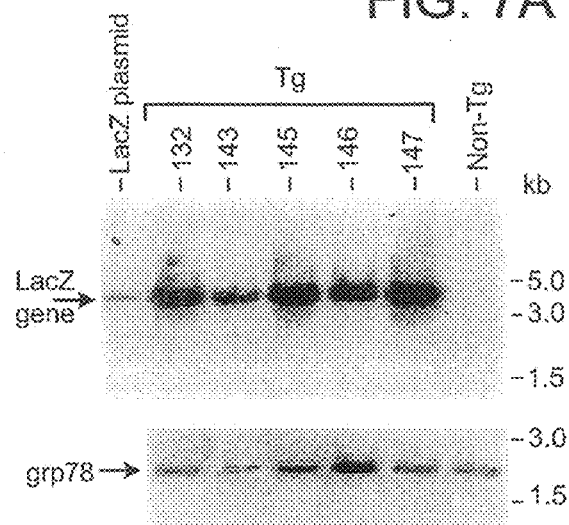
FIG. 7A
FIG. 7B
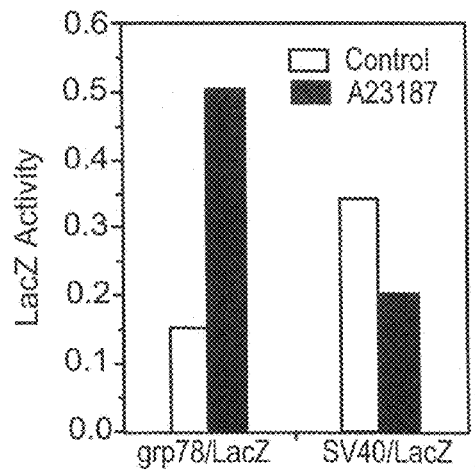
FIG. 7C
FIG. 8

SEQUENCE LISTING

```
<160> NUMBER OF SEQ ID NOS: 1

<210> SEQ ID NO 1
<211> LENGTH: 19
<212> TYPE: DNA
<213> ORGANISM: Artificial Sequence
<220> FEATURE:
<223> OTHER INFORMATION: exemplary motif
<220> FEATURE:
<221> NAME/KEY: misc_feature
<222> LOCATION: (6)...(14)
<223> OTHER INFORMATION: n = A,T,C or G

<400> SEQUENCE: 1
ccaatnnnnn nnnnccacg                                               19
```

STRESS-RESPONSIVE INDUCTION OF A THERAPEUTIC AGENT AND METHODS OF USE

CROSS REFERENCE TO RELATED APPLICATIONS

This application is a divisional of U.S. application Ser. No. 10/928,806, filed on Aug. 27, 2004, now U.S. Pat. No. 7,923,243, which is a continuation of U.S. Application Ser. No. 09/606,804, filed Jun. 28, 2000, now U.S. Pat. No. 7,049,132, which claims priority from U.S. Provisional Application Ser. No. 60/141,505, filed Jun. 28, 1999, the disclosures of which are incorporated herein by reference.

STATEMENT AS TO FEDERALLY-SPONSORED RESEARCH

Pursuant to 35 U.S.C. '202(c), it is acknowledged that the U.S. Government has certain rights in the invention described herein, which was made in part with funds from the National Institutes of Health, Grant Nos. CA27607 and CA59318.

TECHNICAL FIELD

This invention relates to compositions and methods for selective expression of a heterologous nucleic acid sequence in a targeted tissue, and more particularly to the glucose regulated protein 78 (grp78) stress-responsive promoter and its use in gene therapy and the production of transgenic animals.

BACKGROUND

Targeted gene expression is one of the most difficult and important goals in the development effective therapies for a variety of disorders, including, for example, cell proliferative disorders such as cancer or biological stress resulting from glucose starvation in diseases such as diabetes. Two strategies for specific expression include: 1) targetable entry; and 2) tissue or cell type specific gene expression. Targetable entry involves vector engineering to change vector binding tropism thus allowing cell type specific transduction. Tissue or cell specific expression relies on restricting expression of the delivered gene exclusively to a particular type of tissue, such as a tumor.

Successful application of any method for targeting a specific tissue or cell for expression of a particular molecule (e.g., protein or nucleic acid) requires maximization of expression of the molecule in the targeted environment. The most common promoter used to drive expression of a foreign gene has been a constitutive, general-purpose viral promoter such as the MuLV LTR. These promoters, while effective in vitro, often fail to express the sequences under their control within a biologically stressed environment (Palmer et al., Proc. Natl. Acad. Sci. USA, 88:1330, 1991; Gazit et al., Cancer Res., 55:1660, 1995). These data suggest that the MuLV promoter and other constitutive or cellular promoters are not optimal for expressing a nucleic acid sequence within, for example, a fast growing solid tumor devoid of nutrients due to insufficient blood supply. Further, even if a viral promoter escapes genomic silencing, the expression pattern of the foreign gene will be constitutive in normal as well as tumor cells. Such unregulated expression could be highly problematic in gene therapy methods.

To circumvent these difficulties, stress-responsive promoters provide an attractive means for tissue-specific expression of a therapeutic agent. For example, most fast growing tumors have a heterogeneous distribution of blood supply; by having a high interstitial and a low intravascular pressure, a decrease in nutrient supply results, leading to necrosis in the center of the tumor. Glucose deprivation, calcium deprivation, chronic anoxia and low pH known to persist in poorly vascularized solid tumors induce a class of stress proteins referred to as the glucose-regulated proteins (GRPs) (Gazit et al., Cancer Res., 55:1660, 1995; Koong et al., Int. J. Radiat. Oncol. Biol. Phys., 28:661, 1994) including the grp78 gene. A rat grp78 promoter has been used as a potent internal promoter in a retroviral vector to drive expression of the neomycin phosphotransferase (neo) reporter gene in a murine fibrosarcoma model system (Gazit et al., Cancer Res., 55:1660, 1995). Such a promoter provides an attractive means for specifically expressing a therapeutic agent in a biologically stressed tissue using currently available methods in gene therapy.

There are several strategies that have been developed to accomplish gene therapy for the treatment of disorders that give rise to a biologically stressed cellular environment, such as cancer or diabetes, for example. Within these strategies, there is a need for controlled, sustained, site-specific expression of a therapeutic agent such that surrounding healthy tissue remains unaffected by the effects of the therapeutic agent.

SUMMARY

The present invention is based, in part, on the discovery that a stress-responsive promoter specifically drives the expression of a therapeutic agent in vivo resulting in the efficient treatment of a biological stress-related disorder. Accordingly, in one embodiment, the invention provides a nucleic acid construct comprising at least one stress-responsive non-coding regulatory sequence which comprises at least two endoplasmic reticulum stress elements (ERSE) as set forth in SEQ ID NO:1, and a heterologous nucleic acid sequence operatively linked to the regulatory sequence, wherein expression of the heterologous sequence is regulated by the non-coding sequence and wherein the heterologous sequence encodes a therapeutic agent effective for treating a cell proliferative disorder.

In another aspect, the invention provides a nucleic acid construct comprising at least one stress-responsive non-coding regulatory sequence which comprises at least two endoplasmic reticulum stress elements (ERSE) as set forth in SEQ ID NO:1; and a heterologous nucleic acid sequence operatively linked to the regulatory sequence, wherein expression of the heterologous sequence is regulated by the non-coding sequence and wherein the heterologous sequence encodes a detectable marker.

In one aspect, the present invention provides vectors comprising the aforementioned nucleic acid construct.

In another aspect, the present invention provides compositions useful for gene therapy, such as viral vectors comprising a nucleic acid construct of the invention.

The present invention also relates to the use of the before described nucleic acid construct and vectors for the preparation of pharmaceutical compositions for treating, preventing, and/or delaying a disease in a subject, such as, for example, a cell proliferative disease. Furthermore, the recombinant nucleic acid construct and vectors of the invention can be used for the preparation of pharmaceutical compositions for identifying a tumorous disease in a human and non-human animal.

In a further embodiment, the present invention provides cells and transgenic non-human animals, comprising the aforementioned recombinant nucleic acid sequence or vectors stably integrated into their genome and their use for the identification of substances capable of suppressing or activating transcription from a stress-responsive regulatory sequence.

In a further embodiment, the invention provides a method of method for producing a transgenic non-human animal having a phenotype characterized by expression of a heterologous nucleic acid sequence encoding a detectable marker otherwise not naturally occurring in the animal, wherein the heterologous nucleic acid sequence is operably associated with at least one stress-responsive non-coding regulatory sequence comprising at least two endoplasmic reticulum stress elements (ERSE) as set forth in SEQ ID NO:1, the method comprising: a) introducing at least one transgene into a embryo of an animal, the transgene comprising at least one stress-responsive non-coding regulatory sequence comprising at least two endoplasmic reticulum stress elements (ERSE) as set forth in SEQ ID NO:1 isolated upstream from the heterologous nucleic acid sequence encoding a detectable marker; b) transplanting the embryo into a pseudopregnant animal; c) allowing the embryo to develop to term; and d) identifying at least one transgenic offspring containing the transgene.

The details of one or more embodiments of the invention are set forth in the accompanying drawings and the description below. Other features, objects, and advantages of the invention will be apparent from the description and drawings, and from the claims.

DESCRIPTION OF DRAWINGS

The file of this patent contains at least one drawing executed in color. Copies of this patent with color drawing(s) will be provided by the Patent and Trademark Office upon request and payment of the necessary fee.

FIG. 7 shows the presence of the LacZ transgene in transgenic mice. Panel A is a diagram of the grp78/LacZ Transgene construct comprising about 3000 base pairs of the grp78 regulatory sequence operably linked to the LacZ gene. Panel B, upper gel, shows a Southern hybridization resulting in the identification of a LacZ nucleic acid sequence in transgenic animals (Tg 132-147) containing the construct shown in Panel A. In the lower gel, a grp78 cDNA probe which hybridizes to the grp78 gene was used to demonstrate that similar amounts of total DNA were loaded in to each lane of the gel. The transgenic sequences were identified using a suitably labeled LacZ probe. Non-transgenic (Non-Tg) animals do not contain the LacZ sequence. Panel C is a bar graph showing the LacZ activity present in hamster cells tranfected with a plasmid containing a nucleic acid construct shown in panel A (grp78/LacZ) or a plasmid expressing LacZ from the SV40 large T antigen promoter sequence (SV40/LacZ). Cells were treated with the calcium ionophore A23187 to induce biological stress. Untreated and treated activity is indicated.

FIG. 8 shows a diagram of carcinogen treatment of wild-type (+/+), heterozygous for the grp78/LacZ transgene (Tg/+) or homozygous for the grp78/LacZ transgene (Tg/Tg). The carcinogen (7,12-dimethyl benz[a] anthracene) was applied subcutaneously on a weekly basis over a period of six months.

Subsequently, normal and tumorous tissue were isolated and stained for detection of LacZ expression.

Figure 9:
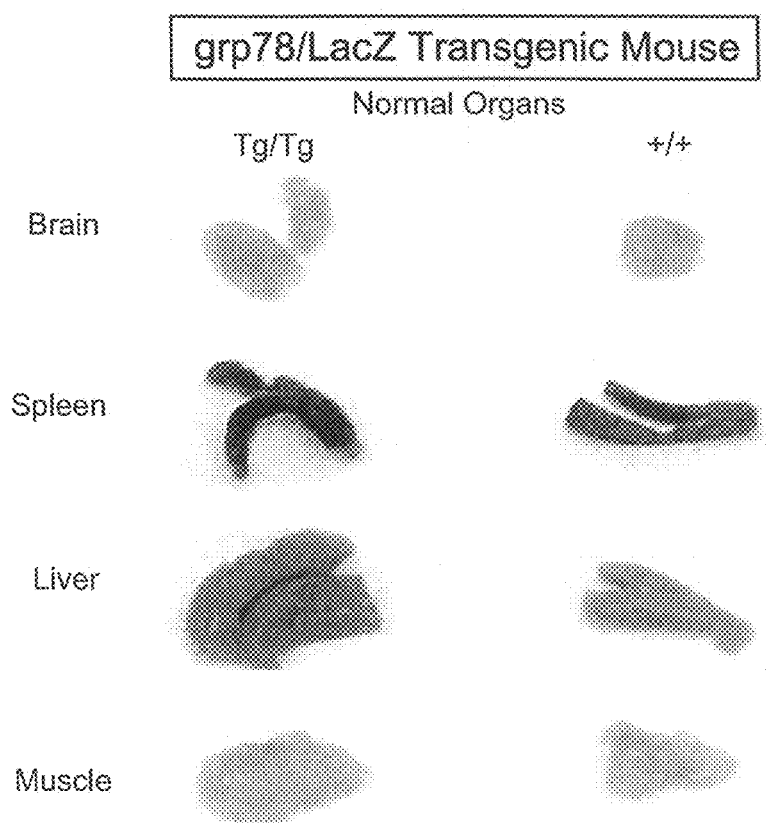

FIG. 9 shows color photographs of normal (non-neoplastic) tissue derived from transgenic mice that are homozygous for the grp78/LacZ transgene (Tg/Tg) or tissue derived from wild-type (non-transgenic) mice (+/+). The mice were treated as described in FIG. 8.

Figure 10:
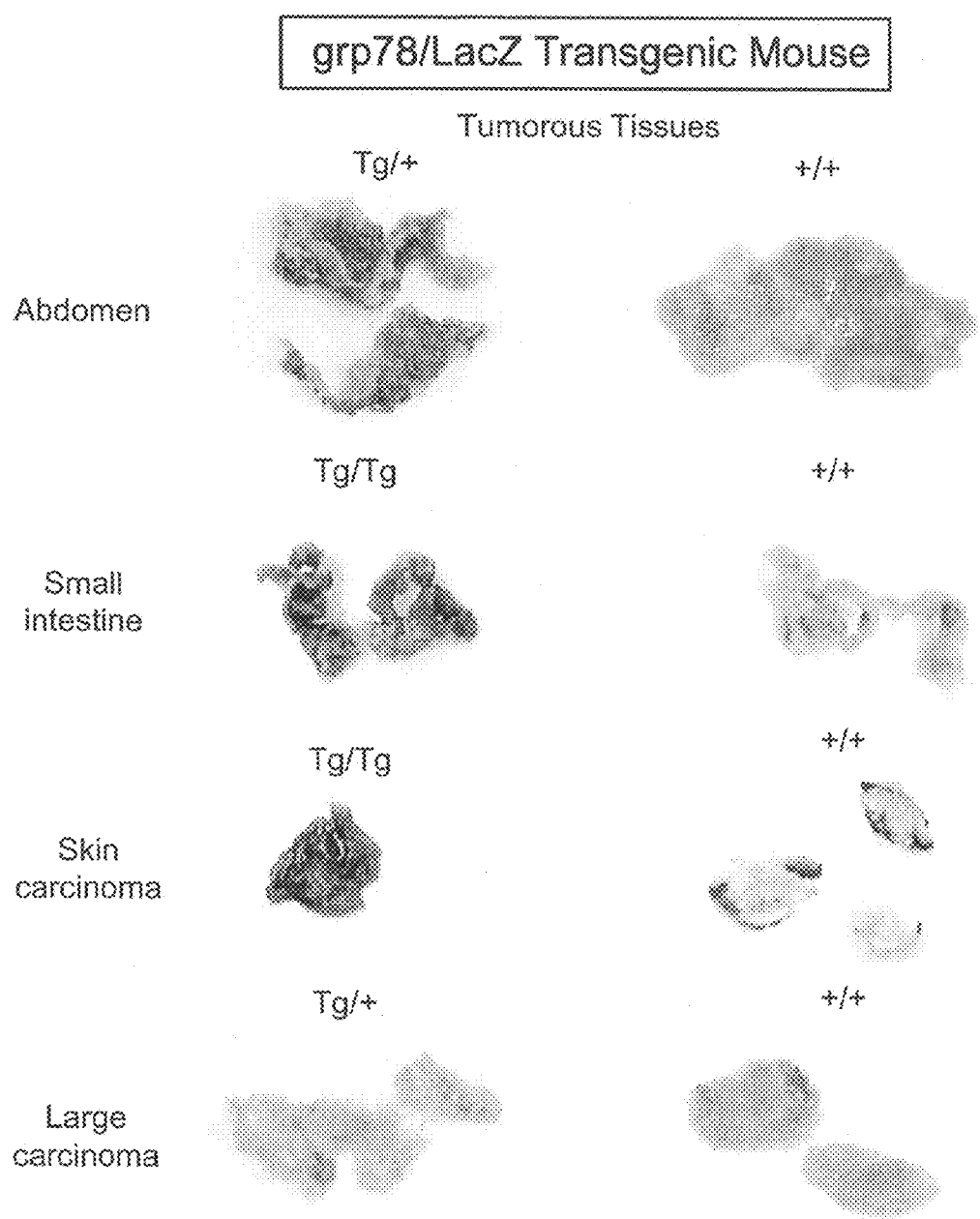

FIG. 10 shows color photographs of tumorous tissues removed from mice treated as described in FIG. 8. Tissue from mice heterozygous for the grp78/LacZ transgene (Tg/+), homozygous for the grp78/LacZ transgene (Tg/Tg) and wild-type (+/+) are indicated. Note that, following LacZ-specific histological staining, LacZ expression is indicated in tumorous tissue derived from Tg/+ mice as well as tissue derived from Tg/Tg mice.

Figure 11:
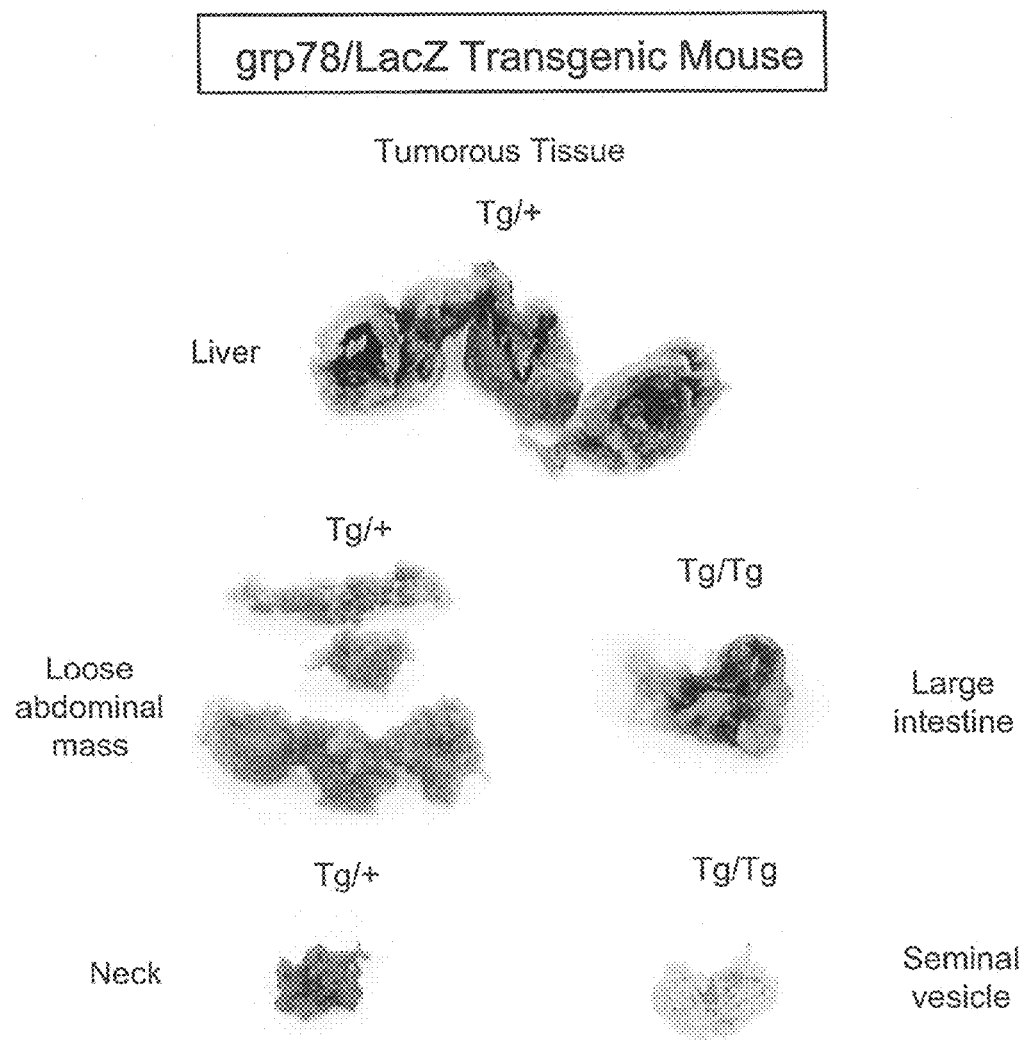

FIG. 11 shows additional color photographs of tumorous tissues removed from mice treated as described in FIG. 8. Tissue from mice heterozygous for the grp78/LacZ transgene (Tg/+) or homozygous for the grp78/LacZ transgene (Tg/Tg) are indicated. Note that, following LacZ-specific histological staining, LacZ expression is indicated in tumorous tissue derived from Tg/+ mice as well as tissue derived from Tg/Tg mice.

Like reference symbols in the various drawings indicate like elements.

DETAILED DESCRIPTION

The present invention is directed to compositions and methods for treating a subject diagnosed as having a condition that can be treated by gene therapy. The invention provides a means and method for delivering at least one stress-responsive non-coding regulatory sequence comprising at least two endoplasmic reticulum stress elements (ERSE) as set forth in SEQ ID NO:1; and a heterologous nucleic acid sequence operatively linked to the regulatory sequence, wherein expression of the heterologous sequence is regulated by the non-coding sequence. The non-coding regulatory sequence comprising the ERSE nucleic acid sequences can be derived, for example, from the transcription regulatory sequence of the glucose responsive protein 78 (grp78) gene. In addition, the invention provides transgenic animals the cells of which are homozygous or heterozygous for the expression of a heterologous nucleic acid sequence driven by a stress-responsive promoter sequence. Such animals are useful, for example, for identifying glucose starved, calcium deprived or hypoxic tissue present in the animal during development or upon exposure to mitogenic compounds, such as carcinogens. Further, such animals can be used as models for the development of techniques for the identification of biologically stressed tissue associated with, for example, cell proliferative disorders, such as cancer or disorders associated with inflammation, such as arthritis.

The identification of endoplasmic reticulum stress elements (ERSE) allows for the development of a nucleic acid construct comprising a stress-responsive regulatory sequence operably associated with a heterologous nucleic acid sequence. Such a construct can be incorporated in, for example, a vector suitable for gene therapy. As used herein, a ERSE nucleic acid sequence derived from a grp78 regulatory sequence means a nucleic acid sequence as set forth in SEQ ID NO:1. It is believed that the ERSE sequence of the invention can be incorporated into any non-coding regulatory sequence that provides appropriate transcriptional and translational initiation regions for expression of a heterologous sequence in an animal cell. Preferably, a non-coding regulatory sequence comprising an ERSE nucleic acid sequence of the invention is derived from the glucose responsive protein 78 (grp78) promoter sequence comprising a sequence from about 3000 base pairs 5' of the site of initiation of transcription of the grp78 coding sequence to about 200 base pairs 3' of the site of initiation of the grp78 coding sequence, constituting a 3200 base pair regulatory region of the grp78 gene.

A construct of the invention can be used in conjunction with a heterologous nucleic acid sequence encoding a therapeutic agent. A therapeutic agent can encode a suicide gene for treating a cell proliferative disorder such as cancer or a therapeutic agent can encode a protein useful for ameliorating the adverse effects of glucose starvation in the cell of a diabetic subject, for example. In addition, the present invention allows for the production of non-human transgenic animals that express a heterologous nucleic acid sequence from a grp78 regulatory sequence. This exemplary animal model provides a system for identifying, for example, factors associated with tissue that is biologically stressed, such as tumorous or inflammatory tissues. As used herein, the term "biologically stressed" includes any cellular environment indicative of cellular distress, damage or trauma resulting in the activation of specific factors that respond to such an environment. For example, a biologically stressed tissue can result in a cellular environment that is glucose starved, calcium deprived, hypoxic, acidic or in a pathological state. Biologically stressed further includes tissue generating free radicals, or tissue that is hot or cold, inflamed or transformed or any other biological state indicative of stressed tissue.

The grp78 gene regulatory sequence is located from about 3000 base pairs 5' of the site of initiation of transcription of the grp78 coding sequence to about 200 base pairs 3' of the site of initiation of the grp78 coding sequence and exhibits strong expression in biologically stressed tissue, such as tissue that is glucose starved or hypoxic. Thus, a nucleic acid construct of the invention can include a 3200 base pair regulatory sequence derived from the grp78 gene. The genetic code for endoplasmic reticulum stress signaling leading to grp gene induction consists of two units of a 19 base pair (bp) sequence motif (CCAAT)N9(CCACG) (SEQ ID NO:1) termed ERSE. This sequence contains a tripartite structure, with a high affinity CBF/NF-Y binding site separated by precisely 9 by of a GC rich sequence motif to a low affinity YY1 binding site. The transcription regulatory sequences further include transcriptional control regions such as TATAA and CAAT box sequences as well as sequences that regulate the tissue specificity (i.e., biologically stressed tissue) of the transcribed product. In the nucleic acid construct of the invention, the ATG start codon is typically provided by the nucleic acid sequence expressing the product of interest. As used herein, a "nucleic acid construct" of the invention includes at least one, or multiple, stress-responsive non-coding regulatory sequences and a heterologous nucleic acid sequence operatively linked to the regulatory sequence, wherein expression of the heterologous sequence is regulated by the non-coding sequence. A nucleic acid construct of the invention can be included in an expression vector. An "expression vector" refers to a plasmid, virus or other vehicle known in the art that has been manipulated by insertion or incorporation of the nucleic acid construct of the invention. The expression vector typically contains an origin of replication, as well as specific genes that allow phenotypic selection of the transformed cells. Vectors suitable for use in the present invention are well known in the art.

As used herein, the term "regulatory sequence" or "regulatory element" refers to a nucleic acid sequence capable of controlling the transcription of an operably associated gene. A regulatory sequence of the invention may include a promoter, an enhancer and/or a silencer, for example. Therefore, placing a gene under the regulatory control of a promoter or a regulatory element means positioning the gene such that the expression of the gene is controlled by the regulatory sequence(s). In general, promoters are found positioned 5' (upstream) of the genes that they control. Thus, in the construction of promoter gene combinations, the promoter is preferably positioned upstream of the gene and at a distance from the transcription start site that approximates the distance between the promoter and the gene it controls in the natural setting. As is known in the art, some variation in this distance can be tolerated without loss of promoter function. Similarly, the preferred positioning of a regulatory element, such as an enhancer, with respect to a heterologous nucleic acid sequence placed under its control reflects its natural position relative to the structural gene it naturally regulates. Enhancers are believed to be relatively position and orientation independent in contrast to promoter elements. The noncoding sequences or intron sequences (e.g., which contain regulatory sequences) that are used in the invention construct are not more than about 9 kbp in length.

Regulatory sequence function during expression of a gene under its regulatory control and can be tested at the transcriptional stage using DNA/RNA and RNA/RNA hybridization assays (e.g., in situ hybridization, nucleic acid hybridization in solution or solid support) and at the translational stage using specific functional assays for the protein synthesized (e.g., by enzymatic activity, by immunoassay of the protein, by in vitro translation of mRNA or expression in microinjected xenopus oocytes).

As used herein, the term "nucleic acid sequence" refers to a polymer of deoxyribonucleotides or ribonucleotides, in the form of a separate fragment or as a component of a larger construct. Nucleic acids expressing the products of interest can be assembled from cDNA fragments or from oligonucleotides which provide a synthetic gene which is capable of being expressed in a recombinant transcriptional unit. Polynucleotide or nucleic acid sequences of the invention include DNA, RNA and cDNA sequences.

Nucleic acid sequences utilized in the invention can be obtained by several methods. For example, the DNA can be isolated using hybridization procedures that are well known in the art. These include, but are not limited to:

(1) hybridization of probes to genomic or cDNA libraries to detect shared nucleotide sequences; (2) antibody screening of expression libraries to detect shared structural features and (3) synthesis by the polymerase chain reaction (PCR). Sequences for specific genes can also be found in GenBank, National Institutes of Health computer database.

The term "heterologous nucleic acid sequence" as used herein refers to at least one structural gene that is operably associated with the regulatory sequence of the invention. The nucleic acid sequence originates in a foreign species, or, in the same species if substantially modified from its original form. For example, the term "heterologous nucleic acid sequence" includes a nucleic acid originating in the same species, where such sequence is operably linked to a regulatory sequence that differs from the natural or wild-type regulatory sequence (e.g., grp78 regulatory sequence). Thus, a non-coding regulatory sequence of the invention can be operatively linked to a heterologous nucleic acid sequence that is regulated by the non-coding sequence.

The term "operably associated" refers to functional linkage between the regulatory sequence and the nucleic acid sequence regulated by the regulatory sequence. The operably linked regulatory sequence controls the expression of the product expressed by the nucleic acid sequence. Alternatively, the functional linkage also includes an enhancer element.

"Promoter" means the minimal nucleotide sequence sufficient to direct transcription. Also included in the invention are those promoter elements that are sufficient to render promoter-dependent nucleic acid sequence expression controllable for cell-type specific, tissue specific, or inducible by external signals or agents; such elements may be located in the 5' or 3' regions of the native gene, or in the introns.

"Gene expression" or "nucleic acid sequence expression" means the process by which a nucleotide sequence undergoes successful transcription and translation such that detectable levels of the delivered nucleotide sequence are expressed in an amount and over a time period so that a functional biological effect is achieved. "Expressible genetic construct" as used herein means a construct that has the grp78 regulatory sequences positioned with a heterologous nucleic acid sequence encoding a desired product, such that the nucleic acid sequence is expressed.

A heterologous nucleic acid sequence of the invention can encode a "therapeutic agent" effective for treating, for example, a cell proliferative disorder or a disorder associated with glucose starvation, such as diabetes. As used herein, a "therapeutic agent" can include a structural gene that encodes a biologically active protein of interest. The term "structural gene" excludes the non-coding regulatory sequence that drives transcription. The structural gene may be derived in whole or in part from any source known to the art, including a plant, a fungus, an animal, a bacterial genome or episome, eukaryotic, nuclear or plasmid DNA, cDNA, viral DNA or chemically synthesized DNA. A structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bound by the appropriate splice junctions. The structural gene may also encode a fusion protein. It is contemplated that introduction into animal tissue of nucleic acid constructs of the invention will include constructions wherein the structural gene and its regulatory sequence are each derived from different animal species.

A structural gene can encode an enzyme, such as a drug-metabolizing enzyme that confers a dominant, negatively selectable phenotype to a cell, such as cell death. Such a gene can encode an enzyme that can convert a non-therapeutically effective compound in to a therapeutically effective compound. For example, the activation of a relatively nontoxic (i.e., non-therapeutically effective) prodrug to a cytotoxic (i.e., therapeutically effective) compound in a specifically targeted tissue can be used to effectively treat a cell proliferative disorder. Enzymes capable of performing such a function include herpes simplex virus (HSV) thymidine kinase, vesicular stomatitis virus (VSV) thymidine kinase, deoxycytidine kinase, cytosine deaminase or nucleoside phosphorylase. Prodrugs converted by the aforementioned enzymes include ganciclovir, acyclovir, 6-methoxypurine arabinoside (Ara-M), cytosine arabinoside or cytarabine (Ara-C), fludarabine, 2-chlorodeoxyadenosine, difluorodeoxycytidine, 5-fluorocytidine and 6-methylpurine-2'-deoxyriboside (MeP-dr).

Because current gene transfer techniques are unable to achieve a satisfactorily high level of transfer efficiency in an in vivo setting, alternative strategies that do not require 100% efficiency of gene transfer have been sought. Two general approaches have evolved that may be effective when only a minority of the tumor cells are transduced: (1) cell-targeted suicide, achieved by directing the synthesis of a toxic metabolite that can permeate the tumor microenvironment, and (2) engineering an immune response to the tumor cells by ectopic cytokine expression or other means for immune recognition or activation.

Examples of genes encoding therapeutic agents that can be used in the invention construct include genes encoding enzymes that convert a prodrug to a toxic metabolite. As noted above, a variety of enzymes are capable of performing such a function, and typically kill cells by activation of a relatively nontoxic prodrug to a cytotoxic form. Greater selectivity in killing malignant cells will be obtained if the transferred gene is not normally found in human beings (e.g., HSV-thymidine kinase), rather than by overexpressing an endogenous gene (e.g., deoxycytidine kinase).

The tumoricidal activity of the HSV-TK/ganciclovir system is due to several factors. In dividing cells, the phosphorylated ganciclovir inhibits DNA synthesis. This effect is not confined to cells that are directly transduced with HSV-TK, as neighboring cells are also affected. This phenomenon, which likely occurs as a result of several mechanisms, has been termed the "bystander effect" and has been observed in several tumor types, including CNS tumors. Transfer of the phosphorylated ganciclovir between cells ("metabolic cooperation") via gap junctions has been proposed as a possible mechanism. Phagocytosis by neighboring cells of ganciclovir phosphate-containing apoptotic vesicles (from dying transduced cells) also has been proposed.

In addition, a therapeutic agent of the invention includes nucleic acid sequences encoding tumor suppressor proteins such as p53 (Takahashi et al. Cancer Res. 62:2340, 1992) and Retinoblastoma (RB); and nucleic acid sequences encoding apoptosis or cell death promoting proteins such as Fas (Itoh et al., Cell 66:233, 1991), GAX (PCT/US95/01882), and FADD (Chinnalyan et al. Cell, 81:505, 1995) which interacts with the death domain of Fas and initiates apoptosis.

A therapeutic agent of the invention also includes nucleic acid sequences that encode cell cycle blockers such as GATA-6 (Suzuki et al, Genomics, 38:283, 1996), anti-angiogenesis proteins such as endostatin and angistatin (Folkman J., Nature Med. 1:27, 1995), anti-sense gene sequences (Wang, Nature Med. 3:887, 1997), and viral subunit vaccines (Donnelly et al. Nature Med. 1:583, 1995).

A therapeutic agent also encompasses those sequences encoding proteins, such as asparaginase, that induce cell death by depriving a cell of a necessary metabolite. Asparaginase induces apoptosis by catalyzing the hydrolysis of circulating asparagine to aspartic acid and ammonia, thus depriving cells of the asparagine necessary for protein synthesis, leading to cell death.

A therapeutic agent of the invention also includes immunomodulators and other biological response modifiers. The term "biological response modifiers" encompasses substances that are involved in modifying the immune response in such manner as to enhance the destruction of tumor, for example. Examples of immune response modifiers include such compounds as lymphokines. Lymphokines include tumor necrosis factor, the interleukins, lymphotoxin, macrophage-activating factor, migration inhibition factor, colony stimulating factor, and interferon. Included in this category are immunopotentiating agents including nucleic acids encoding a number of the cytokines classified as "interleukins". These include, for example, interleukins 1 through 12.

Also included in this category, although not necessarily working according to the same mechanisms, are interferons, and in particular gamma interferon (γ-IFN), tumor necrosis factor (TNF) and granulocyte-macrophage-colony stimulating factor (GM-CSF). Nucleic acids encoding growth factors, toxic peptides, ligands, receptors, suicide factors (e.g., TK) or other physiologically important proteins can also be introduced into specific cells of the prostate.

Further, a therapeutic agent includes sense or antisense nucleic acids encoded by a heterogenous nucleic acid of the invention. For example, a sense polynucleotide sequence (the DNA coding strand) encoding a polypeptide can be introduced into the cell to increase expression of a "normal" gene. Other cell disorders can also be treated with nucleic acid sequences that interfere with expression at the translational level. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme. Alternatively, the method includes administration of a reagent that mimics the action or effect of a gene product or blocks the action of the gene. Therefore, when a cell proliferative disorder, such as cancer, is etiologically linked with over expression of a polynucleotide, it would be desirable to administer an inhibiting reagent such as an antisense polynucleotide. For example, overexpression of the bcl-2 gene that is translocated in nodular non-Hodgkin's lymphomas, inactivates a key pathway of programmed cell death (apoptosis) and leads to continuous proliferation and survival of highly mutated tumor cells that have the capacity to survive DNA damage. Similarly, an increase in expression of the D cyclin (the prad oncogene) promotes cell entry into DNA synthesis. Additional oncogenes that promote cell proliferation include ABL, ERBB-1, ERBB-2 (NEU), GIP, GSP, MYC, L-MYC, N-MYC, H-RAS, RET, ROS, K-SAM, SIS, SRC, C-FOS, C-JUN AND TRK. Thus, efforts directed toward restoring apoptosis in tumor cells, by inhibiting the overexpression of an apoptosis inhibitor, such as bcl-2, or cell proliferation promoting oncogene, such as Ras, can be accomplished using antisense methodology.

The use of antisense methods to inhibit the in vitro translation of genes is well known in the art (see, e.g., Marcus-Sakura, Anal. Biochem., 172:289, 1988). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an RNA molecule (e.g., an mRNA molecule) (see, e.g., Weintraub, Scientific American, 262:40, 1990). The antisense nucleic acids hybridize to corresponding nucleic acids, such as mRNAs, to form a double-stranded molecule, which interferes with translation of the mRNA, as the cell will not translate a double-stranded mRNA. Antisense nucleic acids used in the invention are typically at least 10-12 nucleotides in length, for example, at least 15, 20, 25, 50, 75, or 100 nucleotides in length. The antisense nucleic acid can also be as long as the target nucleic acid with which it is intended to form an inhibitory duplex. As is described further below, the antisense nucleic acids can be introduced into cells as antisense oligonucleotides, or can be produced in a cell in which a nucleic acid encoding the antisense nucleic acid has been introduced by, for example, using gene therapy methods.

Gene Therapy

The present invention also provides gene therapy for the treatment of a cell proliferative disorder. Such therapy would achieve its therapeutic effect by introduction of the nucleic acid construct of the invention into cells having the disorder such that a heterologous nucleic acid sequence encoding a therapeutic agent or a detectable marker is expressed from a stress-responsive non-coding regulatory sequence. Preferably, the regulatory sequence is isolated from a glucose responsive protein 78 (grp78), however any regulatory sequence suitable for expression biologically stressed cells and/or tissue can be used in the present invention.

Delivery of a nucleic acid construct of the invention can be achieved by introducing the construct into a cell using a variety of methods known to those of skill in the art. For example, the construct can be delivered into a cell using a colloidal dispersion system. Alternatively, nucleic acid construct of the invention can be incorporated (i.e., cloned) into an appropriate vector. For example, a recombinant vector of the invention can be an expression vector suitable for expression of the heterologous sequence in a target cell, such as a cell that is biologically stressed. Preferably, a recombinant vector comprising nucleic acid construct of the invention includes a replication competent or replication incompetent recombinant viral vector. For example, a recombinant viral vector of the invention can be derived from an RNA virus (i.e., retrovirus) such s lentivirus, or a DNA virus such as adenovirus. Delivery of a construct of the invention into a cell can be performed in vivo or ex vivo. Further, methods of the invention can be performed alone or in conjunction with standard medical treatments currently available for treating a cell proliferative disorder. For example, when a tumor is being treated, it may be preferable to remove the majority of a tumor surgically or by radiation prior to introducing a construct of the invention in to the cells comprising the tumor.

Various viral vectors that can be utilized for gene therapy, as taught herein, include DNA viruses such as adenovirus, herpes virus, vaccinia, or an RNA virus such as a retrovirus. The retroviral vector can be a derivative of a retrovirus capable of infecting a mammalian host cell. Examples of retroviral vectors in which a foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a nucleic acid construct of the invention into a target cell. By inserting the construct of the invention into the viral vector along with another gene that encodes ligand for a receptor on a specific target cell, for example, the vector is now target cell entry specific as well target cell expression specific. Preferred targeting is accomplished by using an antibody to target the retroviral vector. Those of skill in the art will know of, or can readily ascertain without undue experimentation, specific polynucleotide sequences which can be inserted into the retroviral genome, for example, to allow target specific delivery of the retroviral vector containing the construct of the invention.

Retroviruses are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The family Retroviridae are enveloped single-stranded RNA viruses that typically infect mammals as well as avian species. Retroviruses are unique among RNA viruses in that their multiplication involves the synthesis of a DNA copy of the RNA that is then integrated into the genome of the infected cell.

The Retroviridae family consists of three groups: the spumaviruses (or foamy viruses) such as the human foamy virus (HFV); the lentiviruses, as well as visna virus of sheep; and the oncoviruses (although not all viruses within this group are oncogenic). The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2) and simian immunodeficiency virus (SIV).

Retroviruses are defined by the way in which they replicate their genetic material. During replication the RNA is converted into DNA. Following infection of the cell a double-stranded molecule of DNA is generated from the two molecules of RNA that are carried in the viral particle by the molecular process known as reverse transcription. The DNA form becomes covalently integrated in the host cell genome as a provirus, from which viral RNAs are expressed with the aid of cellular and/or viral factors. The expressed viral RNAs are packaged into particles and released as infectious virion.

Retroviruses can be transmitted horizontally and vertically. Efficient infectious transmission of retroviruses requires the expression on the target cell of receptors that specifically recognize the viral envelope proteins, although viruses may use receptor-independent, nonspecific routes of entry at low efficiency. In addition, the target cell type must be able to support all stages of the replication cycle after virus has bound and penetrated. Vertical transmission occurs when the viral genome becomes integrated in the germ line of the host. The provirus will then be passed from generation to generation as though it were a cellular gene. Hence endogenous proviruses become established which frequently lie latent, but which can become activated when the host is exposed to appropriate agents.

Numerous gene therapy methods that take advantage of retroviral vectors for treating a wide variety of diseases are known in the art (see, e.g., U.S. Pat. Nos. 4,405,712 and 4,650,764; Friedmann, 1989, Science, 244:1275-1281; Mulligan, 1993, Science, 260:926-932, R. Crystal, 1995, Science 270:404-410, each of which are incorporated herein by reference in their entirety). An increasing number of these methods are currently being applied in human clinical trials (Morgan, 1993, BioPharm, 6(1):32-35; see also The Development of Human Gene Therapy, Theodore Friedmann, Ed., Cold Spring Harbor Laboratory Press, Cold Spring Harbor, N.Y., 1999. ISBN 0-87969-528-5, which is incorporated herein by reference in its entirety). The safety of these currently available gene therapy protocols can be substantially increased by using retroviral vectors of the present invention. For example, where the retroviral vector infects a non-targeted cell, the retroviral genome will integrate but the heterologous nucleic acid sequence will not be transcribed unless the cell or tissue is biologically stressed. However, when the retroviral vector containing a nucleic acid construct of the invention infects a targeted cell (i.e., a cell that is glucose starved, calcium deprived, hypoxic, etc.) the activation of the stress-responsive regulatory sequence will result in transcription and translation of the heterologous nucleic acid sequence.

Recombinant retroviruses defective for replication require assistance in order to produce infectious vector particles. This assistance can be provided, for example, by using helper cell lines that contain plasmids encoding all of the structural genes of the retro virus under the control of regulatory sequences within the LTR. These plasmids are missing a nucleotide sequence that enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Another targeted delivery system useful for introducing a nucleic construct of the invention into a target cell is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles that are useful as delivery vehicles in vitro and in vivo. It has been shown that large unilamellar vesicles (LUV), which range in size from 0.2-4.0 um can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In order for a liposome to be an efficient gene transfer vehicle, the following characteristics should be present: (1) encapsulation of the nucleic acid of interest (i.e., a nucleic acid construct of the invention or a vector comprising the construct) at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

In preferred embodiments, the grp78 regulatory sequence comprises at least one stress-responsive nucleic acid sequence regulatable by factors present in biologically stressed cells and tissues such as glucose starved or hypoxic cells or tissue. In one aspect of the invention, the expression of a heterologous nucleic acid sequence encoding a therapeutic agent or detectable marker is regulated by fusion of the heterologous nucleic acid, or a fragment thereof, to at least one stress-responsive regulatory sequence, such as, for example, a grp78 regulatory sequence. A grp78 regulatory sequence is one that is not normally associated with, and does not normally regulate, the expression of a heterologous nucleic acid that it regulates in the practice of the invention. Grp78 regulatory elements can comprise transcriptional, post-transcriptional, translational, and post-translational elements; as well as regulatory elements related to replication. By way of example, grp78 transcriptional regulatory elements can include promoters, enhancers, operators, and elements that modulate the rate of transcription initiation, elongation and/or termination; post-transcriptional regulatory elements can include those influencing messenger stability, processing and transport; translational regulatory elements can include those which modulate the frequency of translation initiation and the rate of translational elongation; post-translational regulatory elements can include those which influence protein processing, stability and transport; and replication-associated regulatory elements can include those related to gene dosage.

In one embodiment, the invention provides recombinant vectors comprising a nucleic acid construct of the invention. The recombinant vectors are made using standard methods of molecular biology and biotechnology to incorporate a nucleic acid construct of the invention containing a heterologous nucleic acid sequence in operative linkage with a stress-responsive regulatory sequence, such as a grp-78 regulatory sequence. In preferred embodiments, the grp-78 regulatory sequence will be upstream of the heterologous sequence when they are placed in operative linkage. Locations of restriction enzyme recognition sequences can be easily determined by one of skill in the art. Alternatively, various in vitro techniques can be used for insertion of a restriction enzyme recognition sequence at a particular site, or for insertion of nucleic acid construct at a site that does not contain a restriction enzyme recognition sequence. Such methods include, but are not limited to, oligonucleotide-mediated heteroduplex formation for insertion of one or more restriction enzyme recognition sequences (see, for example, Zoller et al. (1982) Nucleic Acids Res. 10:6487-6500; Brennan et al. (1990) Roux's Arch. Dev. Biol. 199:89-96; and Kunkel et al. (1987) Meth. Enzymology 154:367-382) and PCR-mediated methods for insertion of longer sequences. See, for example, Zheng et al. (1994) Virus Research 31:163-186.

Operative linkage refers to an arrangement of one or more regulatory sequences with one or more coding sequences, such that the regulatory sequence(s) is capable of exerting its regulatory effect on the coding sequence.

By way of illustration, a stress responsive-transcriptional regulatory sequence or a promoter is operably linked to a heterologous sequence if the transcriptional regulatory sequence or promoter promotes transcription of the heterologous sequence. Similarly, an operator is considered operatively linked to a promoter or to a heterologous sequence if binding of a repressor to the operator inhibits initiation at the promoter so as to prevent or diminish expression of the heterologous sequence. An operably linked transcriptional regulatory sequence is generally joined in cis with the coding sequence, but it is not necessarily directly adjacent to it.

Recombinant vectors comprising a nucleic acid construct of the invention can also comprise other types of sequence including, but not limited to, replication origins, detectable markers (including, but not limited to, those encoding antibiotic resistance), transcription termination sites, sequences specifying translation initiation and termination, sequences mediating mRNA processing and/or stability and multiple cloning sites.

Recombinant vectors can exist as freely-replicating extrachromosomal elements, such as plasmids or episomes, or can exist as chromosomal recombinants, such as would be achieved either by integration of a nucleic acid construct into the chromosome of a cell. Methods for obtaining chromosomal integration of recombinant vectors have been described, for example, by Gerhardt et al., METHODS FOR GENERAL AND MOLECULAR MICROBIOLOGY, American Society for Microbiology, Washington, D.C., 1994; Link et al. (1997) J. Bacteriol. 179:6228-6237; and Metcalf et al. (1996) Plasmid 35:1-13.

A coding sequence, as present in a recombinant construct, can encode a full-length nucleic product (i.e., the length normally found in the wild-type cell) or any fragment of a gene product. A gene product can be RNA or a polypeptide; untranslated RNA gene products can include structural, catalytic and regulatory RNA molecules. Examples of untranslated RNA gene products include, but are not limited to, tRNA, rRNA, antisense RNAs and ribozymes. In one embodiment, a coding sequence comprises a gene, which can encode a therapeutic agent, or a gene product whose function is to act as a detectable marker under a particular set of environmental conditions. It is understood that any gene of interest can be placed in operative linkage with grp-78 regulatory region sequences, so that its expression is regulated by the grp78 regulatory region sequences.

The phrase "non-dividing" cell refers to a cell that does not go through mitosis. Non-dividing cells may be blocked at any point in the cell cycle, (e.g., G0/G1, G1/S, G2/M), as long as the cell is not actively dividing. For ex vivo infection, a dividing cell can be treated to block cell division by standard techniques used by those of skill in the art, including, irradiation, aphidocolin treatment, serum starvation, and contact inhibition. However, it should be understood that ex vivo infection is often performed without blocking the cells since many cells are already arrested (e.g., stem cells). For example, a recombinant lentivirus vector of the invention is capable of infecting any non-dividing cell, regardless of the mechanism used to block cell division or the point in the cell cycle at which the cell is blocked. Examples of pre-existing non-dividing cells in the body include neuronal, muscle, liver, skin, heart, lung, and bone marrow cells, and their derivatives. For dividing cells onco-retroviral vectors can be used.

By "dividing" cell is meant a cell that undergoes active mitosis, or meiosis. Such dividing cells include stem cells, skin cells (e.g., fibroblasts and keratinocytes), gametes, and other dividing cells known in the art. Of particular interest and encompassed by the term dividing cell are cells having cell proliferative disorders, such as neoplastic cells. The term "cell proliferative disorder" refers to a condition characterized by an abnormal number of cells. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well.

The present invention provides gene therapy for the treatment of cell proliferative disorders or disorders associated with glucose starvation such as diabetes. Such therapy would achieve its therapeutic effect by introduction of a nucleic acid construct encoding an appropriate therapeutic agent (e.g., suicide gene, tumor suppressor genes, antisense, ribozymes), into cells of subject having the disorder. Delivery of such a nucleic acid constructs can be achieved using a viral vector of the present invention.

Cell proliferative disorders include disorders associated with an overgrowth of connective tissues, such as various fibrotic conditions, including scleroderma, arthritis and liver cirrhosis. Cell proliferative disorders include neoplastic disorders such as head and neck carcinomas. Head and neck carcinomas would include, for example, carcinoma of the mouth, esophagus, throat, larynx, thyroid gland, tongue, lips, salivary glands, nose, paranasal sinuses, nasopharynx, superior nasal vault and sinus tumors, esthesioneuroblastoma, squamous call cancer, malignant melanoma, sinonasal undifferentiated carcinoma (SNUC) or blood neoplasia. Also included are carcinoma's of the regional lymph nodes including cervical lymph nodes, prelaryngeal lymph nodes, pulmonary juxtaesophageal lymph nodes and submandibular lymph nodes (Harrison's Principles of Internal Medicine (eds., Isselbacher, et al., McGraw-Hill, Inc., 13th Edition, pp 1850-1853, 1994). Other cancer types, include, but are not limited to, lung cancer, colon-rectum cancer, breast cancer, prostate cancer, urinary tract cancer, uterine cancer lymphoma, oral cancer, pancreatic cancer, leukemia, melanoma, stomach cancer and ovarian cancer.

Disorders associated with glucose starvation include diabetes or any other disorder wherein tissue is constantly or periodically subjected to low glucose availability such that the cells of the tissue are biologically stressed.

In addition, the therapeutic methods (e.g., the gene therapy or gene delivery methods) as described herein can be performed in vivo or ex vivo. It may be preferable to remove the majority of a tumor prior to gene therapy, for example surgically or by radiation.

The invention also provides a method of nucleic acid transfer to a target cell to provide expression of a particular nucleic acid sequence (e.g., a heterologous sequence). Therefore, in another embodiment, the invention provides a method for introduction and expression of a heterologous nucleic acid sequence in a target cell comprising infecting the target cell with a recombinant virus of the invention containing a nucleic acid construct of the invention and expressing the heterologous nucleic acid sequence in the target cell. As mentioned above, the target cell can be any cell type including dividing, non-dividing, neoplastic, immortalized, modified and other cell types recognized by those of skill in the art, so long as they are capable of infection by a retrovirus.

In another embodiment, the invention provides a method of treating a subject having a cell proliferative disorder. The subject can be any mammal, and is preferably a human. The subject is contacted with a recombinant vector of the present invention. The recombinant vector is preferably a recombinant viral vector and more preferably a recombinant retroviral vector. The contacting can be in vivo or ex vivo. Methods of administering the vector of the invention are known in the art and include, for example, systemic administration, topical administration, intraperitoneal administration, intra-muscular administration, as well as administration directly at the site of a tumor or cell-proliferative disorder and other routes of administration known in the art.

Pharmaceutical Compositions

The invention further includes various pharmaceutical compositions useful for treating a cell proliferative disorder or a disorder associated with glucose starvation such as, for example, diabetes. The present invention provides a nucleic acid construct capable of driving the expression of a therapeutic agent in a cell associated with biologically stressed tissue.

A biologically stressed tissue of the invention includes those tissues where the cellular environment is "naturally" glucose starved, calcium deprived, hypoxic, acidic or in a pathological state. Biologically stressed further includes tissue generating free radicals, or tissue that is hot or cold, inflamed or transformed or any other biological state indicative of stressed tissue. A naturally biologically stressed tissue is a tissue wherein normal cellular metabolism in conjunction with a pathological state has induced the biological stress. For example, a fast growing solid tumor devoid of nutrients due to insufficient blood supply exposes the neoplastic cells contained in such an environment to glucose deprivation, calcium deprivation, chronic anoxia and low pH. Thus, the cells in such an environment are subjected to biological stress that is induced by a pathological state resulting from tumor growth. The nucleic acid construct of the invention can be used to express a therapeutic agent, such as, for example, a suicide gene, or an apoptosis-inducing gene, such that the targeted cell is killed. The surrounding healthy tissue remains unaffected by the treatment because they do not provide a biologically stressed necessary for expression of the therapeutic agent.

In addition, diabetes is a disease that results in glucose starvation in a wide range of tissues. Cells subjected to glucose deprivation must utilize other sources of energy in order to survive. The consequences of this type metabolism is a cellular environment that is, for example, acidic. Again, a nucleic acid construct of the invention can be used to express a therapeutic agent such that the acidic environment of a targeted cell can be ameliorated by expression of the agent.

A biologically stressed tissue of the invention also includes those tissues where a biologically stressed cellular environment has been "artificially" induced. For example, photodynamic therapy involves the combined use of photosensitizing drugs and light for the treatment of malignant or benign disease. The photosensitized chemical reaction requires oxygen. Light, delivered to the tissue, activates porphyrin molecules. These molecules transfer their energy to form cytotoxic singlet oxygen, which results in lethal alteration of cellular membranes and subsequent tissue destruction. Artificial means for inducing biological stress also include compounds such as combretastatin A4-phosphate (CA4DP). CA4DP has been used as an antiangiogenesis agent to prevent or reduce the blood supply to, for example, tumorous tissue. Reduced blood supply facilitated by CA4DP, or any other antiangiogenic agent, promotes biological stress in the affected tissue and provides the appropriate environment for expression of a therapeutic agent of the invention.

Thus, a nucleic acid construct of the invention can be used in conjunction with a method for "artificially" inducing a biologically stressed cellular environment. For example, the construct can be introduced into a cell as part of a pharmaceutical composition comprising, for example, a liposomal delivery vehicle or a viral delivery vehicle, prior to, during, or subsequent to artificial induction of biological stress. Potential uses in dermatology include the treatment of malignant cutaneous lesions and nononcologic conditions, including psoriasis, alopecia, viral infections, and vascular malformations. Photodynamic therapy also has been employed for bladder, endobronchial, and esophageal carcinoma.

The pharmaceutical compositions according to the invention are prepared by placing a nucleic acid construct of the invention into a form suitable for administration to a subject using carriers, excipients and additives or auxiliaries. The nucleic acid construct can be contained in a recombinant vector, preferably a recombinant viral vector and most preferably a recombinant retroviral vector. A pharmaceutical composition can include a nucleic acid construct of the invention comprising at least one stress-responsive non-coding regulatory sequence comprising at least two endoplasmic reticulum stress elements (ERSE). Preferably, the stress-responsive non-coding regulatory sequence is derived from a glucose responsive protein 78 (grp78) gene. A heterologous nucleic acid sequence operatively linked to the regulatory sequence. The expression of the heterologous sequence is regulated by the non-coding sequence and the heterologous sequence can encode a therapeutic agent effective for treating, for example, a cell proliferative disorder.

Generally, the terms "treating", "treatment", and the like are used herein to mean obtaining a desired pharmacologic and/or physiologic effect. The effect may be therapeutic in terms of a partial or complete cure for a cell proliferative disorder. "Treating" as used herein covers any treatment of (e.g., complete or partial), or prevention of, a cell proliferation disorder or for ameliorating the pathogenic effect of biological stress, such as biological stress induced by glucose deprivation, in a mammal, particularly a human, and includes:

(a) preventing the disease from occurring in a subject that may be predisposed to the disease, but has not yet been diagnosed as having it;
(b) inhibiting the disorder, i.e., arresting the development of, for example, a tumor; or
(c) relieving or ameliorating the disorder or disease, i.e., cause regression of the disorder or disease.

Thus, the invention includes various pharmaceutical compositions useful for ameliorating symptoms attributable to a cell proliferative disorder or, alternatively, for inducing a protective immune response to treat a cell proliferative disorder or for ameliorating the pathogenic effect of biological stress. For example, a pharmaceutical composition according to the invention can be prepared to include a nucleic acid construct according to the invention into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences,* 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's *The Pharmacological Basis for Therapeutics* (7th ed.).

The pharmaceutical compositions according to the invention may be administered locally or systemically. By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Langer, *Science,* 249: 1527, (1990); Gilman et al. (eds.) (1990), each of which is herein incorporated by reference.

As used herein, "administering a therapeutically effective amount" is intended to include methods of giving or applying a pharmaceutical composition of the invention to a subject that allow the composition to perform its intended therapeutic function. The therapeutically effective amounts will vary according to factors such as the degree of infection in a subject, the age, sex, and weight of the individual. Dosage regima can be adjusted to provide the optimum therapeutic response. For example, several divided doses can be administered daily or the dose can be proportionally reduced as indicated by the exigencies of the therapeutic situation.

The pharmaceutical composition can be administered in a convenient manner such as by injection (subcutaneous, intravenous, etc.), oral administration, inhalation, transdermal application, or rectal administration. Depending on the route of administration, the pharmaceutical composition can be coated with a material to protect the pharmaceutical composition from the action of enzymes, acids and other natural conditions that may inactivate the pharmaceutical composition. The pharmaceutical composition can also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle which contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft shell gelatin capsule, compressed into tablets, or incorporated directly into the individual's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5 to about 80% of the weight of the unit.

The tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the agent, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the pharmaceutical composition can be incorporated into sustained-release preparations and formulations.

As used herein, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the individual to be treated; each unit containing a predetermined quantity of pharmaceutical composition is calculated to produce the desired therapeutic effect in association with the required pharmaceutical carrier. The specification for the novel dosage unit forms of the invention are dictated by and directly dependent on (a) the unique characteristics of the pharmaceutical composition and the particular therapeutic effect to be achieve, and (b) the limitations inherent in the art of compounding such an pharmaceutical composition for the treatment of a pathogenic infection in a subject.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

Transgenic Animal Production

Transgenesis is a term used to describe the artificial introduction of new genetic material into the germ line of an organism. As such, it is a form of genetic manipulation that includes not only the introduction of foreign DNA into the germ line but also designer gene modifications which to date usually involve the insertion of new extraneous DNA. Transgenic animals are useful as models for diseases for the testing of pharmacological agents prior to clinical trials or the testing of therapeutic modalities.

Thus, in another embodiment, the present invention provides a transgenic non-human animal containing a nucleic acid construct of the invention. As previously noted, a "nucleic acid construct" of the invention includes at least one, or multiple, stress-responsive non-coding regulatory sequences and a heterologous nucleic acid sequence operatively linked to the regulatory sequence, wherein expression of the heterologous sequence is regulated by the non-coding sequence. Thus, a "transgene", as used herein, refers to a nucleic acid construct of the invention that is inserted by artifice into a cell, and becomes part of the genome of the organism that develops from that cell. For example, a transgene of the present invention can contain multiple grp78 regulatory elements driving expression of a heterologous nucleic acid sequence in biologically stressed tissue, such as glucose starved or hypoxic tissue.

Phenotypically, a transgenic animal of the present invention can appear normal because of the unique stress-responsive regulatory sequence used to develop the animal. Such a promoter is fully active only in a cellular environment that exhibits the biochemical manifestations of biological stress. As previously noted, such a cellular environment can include, but is not limited to, glucose starvation, calcium deprivation or hypoxia. Thus, a transgene of the present invention may not be active under normal cellular conditions. However, when an animal having such a transgene incorporated in to its genome is exposed to conditions that induce biological stress in the whole animal or in specific tissues, the transgene can become activated in the whole animal or only in specific tissues. For example, exposure of a transgenic animal of the invention to a mitogenic agent can induce a cell proliferative disorder such that a tumor develops as a result of the exposure. As previously noted, a fast growing solid tumor devoid of nutrients due to insufficient blood supply exposes the neoplastic cells contained in such an environment to glucose deprivation, calcium deprivation, chronic anoxia and low pH. Thus, a transgene containing a stress-responsive regulatory sequence, such as grp78, can become active in this environment.

The present invention provides transgenic animals that are heterozygous for the transgene and animals that are homozygous for the transgene of the invention. As shown in FIGS. 10 and 11, both heterozygous and homozygous animals display activity of the stress responsive regulatory sequence in tissues that have developed tumors, i.e. are biologically stressed. Thus, it is understood that both heterozygous and homozygous transgenic animals of the invention are useful, for example, for identifying compounds that induce biological stress in such an animal.

A transgene of the invention includes a nucleic acid construct comprising at least one stress-responsive regulatory sequence operably associated with a heterologous nucleic acid sequence. A heterologous nucleic acid sequence can encode a detectable marker expressed under the control of a stress-responsive regulatory sequence that is active in a targeted, biologically stressed, tissue. For example, grp78 regulatory sequences can be used in conjunction with a heterologous nucleic acid sequence encoding a visually detectable marker, such as green fluorescent protein (GFP), or a biologically active protein detectable by antibodies or enzymatic assay, to provide a means for identifying biologically stressed tissue in a transgenic animal. A heterogenous nucleic acid can further include antisense polynucleotides and dominant negative encoding polynucleotides, which may be expressed in a transgenic non-human animal.

The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by expression of antisense nucleic acid. As used herein, the term "transgenic" includes any transgenic technology familiar to those in the art which can produce an organism carrying an introduced transgene or one in which an endogenous gene has been rendered non-functional or "knocked out".

The "non-human animals" of the invention include vertebrates such as rodents, non-human primates, sheep, dog, cow, pig, amphibians, and reptiles. Preferred non-human animals are selected from the rodent family including rat and mouse, most preferably mouse. The "transgenic non-human animals" of the invention are produced by introducing "transgenes" into the germline of the non-human animal. Embryonal target cells at various developmental stages can be used to introduce transgenes. As previously noted, different methods are used depending on the stage of development of the embryonal target cell.

A "transgenic" animal can be produced by cross-breeding two chimeric animals which include exogenous genetic material within cells used in reproduction. Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. The use of a one cell embryo as a target for gene transfer has a major advantage in that in most cases the injected DNA will be incorporated into the host gene before the first cleavage (Brinster et al., Proc. Natl. Acad. Sci. USA 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of such an embryo is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retro viral infection (Jaenich, R., Proc. Natl. Acad. Sci. USA 73:1260-1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., Proc. Natl. Acad. Sci. USA 82:6927-6931, 1985; Van der Putten, et al., Proc. Natl. Acad. Sci. USA 82:6148-6152, 1985). Transfection is easily and efficiently obtained by culturing the blastomeres on a monolayer of virus-producing cells (Van der Putten, supra; Stewart, et al., EMBO J. 6:383-388, 1987). Alternatively, infection can be performed at a later stage. Virus or virus-producing cells can be injected into the blastocoele (D. Jahner et al., Nature 298:623-628, 1982). Most of the founders will be mosaic for the transgene since incorporation occurs only in a subset of the cells that formed the transgenic nonhuman animal. Further, the founder may contain various retroviral insertions of the transgene at different positions in the genome that generally will segregate in the offspring. In addition, it is also possible to introduce transgenes into the germ line, albeit with low efficiency, by intrauterine retro viral infection of the midgestation embryo (D. Jahner et al., supra). Methods to make transgenic animals described generally above are described in U.S. Pat. No. 5,162,215, incorporated herein by reference.

In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191, incorporated herein by reference. ES cells are obtained from pre-implantation embryos cultured in vitro and fused with embryos (M. J. Evans et al. Nature 292:154-156, 1981; M. O. Bradley et al., Nature 309: 255-258, 1984; Gossler, et al., Proc. Natl. Acad. Sci. USA 83: 9065-9069, 1986; and Robertson et al., Nature 322:445-448, 1986). Transgenes can be efficiently introduced into the ES cells by as described above. Such transformed ES cells can thereafter be combined with blastocysts from a nonhuman animal.

The analysis of expression of a transgene is essential in determining the utility of the transgenic animal produced. As with integration analysis, the presence or absence of similar or identical endogenous counterparts will determine, to a degree, the strategies that may be most useful. For transgenes that are unique (no endogenous counterpart) or contain some unique sequences, the strategies that can be used are more straightforward. The presence of a novel RNA transcript or a unique protein (or enzyme activity) is more easily determined than it is when the transcript or protein products are very similar to endogeneous transcripts or proteins. As with integration analysis, molecular "tags" are also sometimes useful in that the transcripts will contain some unique identifying sequence that can be readily and unequivocally determined.

A nucleic acid construct of the invention can comprise a suitable detectable marker expressed under the control of a stress-responsive regulatory sequence that is active in a targeted, biologically stressed, tissue. "Detectable marker", as used herein, refers to any identifiable composition useful for distinguishing cells containing a nucleic acid construct of the present invention from those cells that do not contain such a construct.

It is also envisioned that biologically stressed tissue of a transgenic animal of the invention can be identified by the presence of a biologically active protein product encoded by the construct of the invention. Thus, a detectable marker of the invention also includes biologically active protein products. The term "biologically active protein product", as used herein, refers to products produced or synthesized by a host cell as a result of the insertion of a transgene into the cell. In the present example, the cell can be part of a transgenic animal. In addition, the term encompasses those biological products that are secondary products of the activity encoded by a transgene.

In those cases where it is desirable for the detectable marker to encode a biologically active protein product, it is envisioned that antibodies can be used to detect the presence of an antigenic determinant resulting from expression of the protein encoded by the heterologous DNA sequence. Such antibodies may, for example, recognize a specific epitope unique to the expressed protein. The term "epitope", as used herein, refers to an antigenic determinant on an antigen, such as a protein encoded by the heterologous nucleic acid, to which the paratope of an antibody, such as a protein encoded by the heterologous nucleic acid, binds. Antigenic determinants usually consist of chemically active surface groupings of molecules, such as amino acids or sugar side chains, and can have specific three-dimensional structural characteristics, as well as specific charge characteristics.

An antibody suitable for binding to a protein encoded by the heterologous nucleic acid is specific for at least one portion of an extracellular region of the protein encoded by the heterologous nucleic acid polypeptide. For example, one of skill in the art can use the peptides to generate appropriate antibodies of the invention. Antibodies of the invention include polyclonal antibodies, monoclonal antibodies, and fragments of polyclonal and monoclonal antibodies.

The preparation of polyclonal antibodies is well-known to those skilled in the art. See, for example, Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992), which are hereby incorporated by reference. The preparation of monoclonal antibodies likewise is conventional. See, for example, Kohler & Milstein, Nature 256:495 (1975); Coligan et al., sections 2.5.1-2.6.7; and Harlow et al., Antibodies: A Laboratory Manual, page 726 (Cold Spring Harbor Pub. 1988), which are hereby incorporated by reference.

In addition, a detectable marker of the invention can be, for example, a visually detectable marker. In one embodiment, the invention utilizes a visually detectable marker protein that fluoresces directly upon illumination with light of an appropriate wavelength. Any fluorescent protein can be used in the invention, including proteins that fluoresce due to intramolecular rearrangements or the addition of cofactors that promote fluorescence. For example, green fluorescent proteins of cnidarians, which act as their energy-transfer acceptors in bioluminescence, are suitable fluorescent proteins for use in the fluorescent indicators. A green fluorescent protein ("GFP") is a protein that emits green light, and a blue fluorescent protein ("BFP") is a protein that emits blue light. GFPs have been isolated from the Pacific Northwest jellyfish, *Aequorea victoria*, the sea pansy, *Renilla reniformis*, and *Phialidium gregarium*. See, Ward, W. W., et al., Photochem. Photobiol., 35:803, 1982); and Levine, L. D., et al., Comp. Biochem. Physiol., 72B:771982.

A variety of *Aequorea*-related GFPs having useful excitation and emission spectra have been engineered by modifying the amino acid sequence of a naturally occurring GFP from *Aequorea victoria*. (See, Prasher, D. C., et al., Gene, 111:229, 1992); Heim, R., et al., Proc. Natl. Acad. Sci., USA, 91:12501, 1994); U.S. Pat. Nos. 5,491,084; 5,625,048, incorporated herein by reference). The cDNA of GFP can be concatenated with those encoding many other proteins; the resulting chimerics often are fluorescent and retain the biochemical features of the partner proteins. (See, Cubitt, A. B., et al., Trends Biochem. Sci. 20:448, 1995). Mutagenesis studies have produced may GFP mutants, some having shifted wavelengths of excitation or emission. Such proteins are included in the invention sensor.

A fluorescent protein is an "*Aequorea*-related fluorescent protein" if any contiguous sequence of 150 amino acids of the fluorescent protein has at least 85% sequence identity with an amino acid sequence, either contiguous or non-contiguous, from the wild type *Aequorea* green fluorescent protein. More preferably, a fluorescent protein is an *Aequorea*-related fluorescent protein if any contiguous sequence of 200 amino acids of the fluorescent protein has at least 95% sequence identity with an amino acid sequence, either contiguous or non-contiguous, from the wild type *Aequorea* green fluorescent protein. Similarly, the fluorescent protein can be related to *Renilla* or *Phialidium* wild-type fluorescent proteins using the same standards.

Other selectable markers include DNA sequences encoding membrane bound polypeptides. Such polypeptides are well known to those skilled in the art and contain a secretory sequence, an extracellular domain, a transmembrane domain and an intracellular domain. When expressed as a positive selection marker, such polypeptides associate with the target cell membrane. Fluorescently labeled antibodies specific for the extracellular domain may then be used in a fluorescence activated cell sorter (FACS) to select for cells expressing the membrane bound polypeptide.

It may also be useful in some circumstances to use a version of a detectable marker that is targeted to a specific subcellular compartment. "Targeting signal sequence", as used herein, refers to any nucleic acid or amino acid sequence useful for predetermining the intracellular or extracellular location of a molecule containing such a sequence. Subcellular targeting of the detectable marker would be achieved by fusing the marker gene to a targeting sequence. For example, the nuclear localization signal from SV40 T antigen could be fused to, for example, a visually detectable marker such as GFP, which would lead to an accumulation of GFP in the nucleus. Numerous subcellular targeting sequences are known in the art. Using this well-known method, GFP has been targeted to subcellular locations including the nucleus, the mitochondria, the cell membrane, nuclear pores, the actin cytoskeleton, the golgi apparatus, transport vescicles and other locations.

The use of a targeting signal sequence is advantageous for three reasons. First, concentration of the detectable marker in a smaller area within the cell gives a brighter, more easily visualized fluorescent signal. Second, some cells tend to exhibit a basal level of background autofluorescence, which is generally distributed throughout the cytoplasm. Targeting GFP, for example, to a specific subcellular location permits the fluorescent signal generated by the transgene to be more easily distinguished from background autofluorescence. A third advantage of using subcellular targeting is that it allows sequential integration of different vector DNAs. This might be desirable in situations when it is desirable to have more than one gene expressed in a transgenic animal. For example, it might be desirable to express a specific monoclonal antibody in a transgenic animal. In this case, a first vector DNA expressing the heavy chain of a desirable antibody could be integrated using GFP fused to an actin cytoskeletal targeting sequence. A second vector DNA carrying a GFP fusion to a nuclear localization signal and a light chain expression cassette could then be integrated. Another example of when this technique might be useful is in the case of proteins that must be processed by a particular protease in order to attain their mature, active forms.

Materials and Methods

Cell Culture Conditions. The tumor cell line B/C10ME was cultured in high glucose Dulbecco's modified Eagle's medium (DMEM) containing 4.5 mg/ml glucose supplemented with 10% fetal calf serum, 2 mM glutamine, and 1% penicillin-streptomycin-neomycin antibiotics. Transduced B/C10ME cells were maintained in 2 mg/ml of G418 respectively. To generate individual transduced clones, transduced cells were plated into 96 well plates by serial dilution, to a final concentration of 0.3 cell/well. Individual clones were then isolated and expanded.

Retroviral Vector Construction. The G1TkSvNa retroviral construct (Lyons et al., Cancer Gene Ther., 2:273, 1995) was obtained from Genetic Therapy Inc./Novartis (Summit, N.J.). G1NaGrpTk (FIG. 1) was constructed by removing the 356 by SV40 promoter region of a retroviral vector G1NaSvTk (Hung et al., Int. J. Pediatr. Oncol., 4:317, 1997) by SalI and BglII and replaced with a 695 by rat grp78 promoter spanning -520 to +175 (Chang et al., Proc. Natl. Acad. Sci. USA, 84:684, 1987). Retroviral vector plasmid DNA was prepared by Qiagen Maxi Kit and transfected into ecotropic retroviral producer cell line PE501. The viral supernatant was harvested and an amphotropic retroviral producer cell line PA317 was transduced and drug (G418) resistant clones were selected. Retroviral vectors were collected and titered by NIH3T3 cells.

Western Blot. For the detection of HSVTK, GRP78 and β-actin, 20 mg of cell lysate were prepared as previously described (Zhou et al., J. Natl. Cancer Inst., 90:381, 1998) and resolved on a denaturing sodium dodecyl sulphate-8% polyacrylamide gel and transferred onto Hybond nitrocellulose membrane (Amersham Life Science Inc., Arlington Heights, Ill.). The membrane was blocked with 5% non-fat milk (Bio-Rad Laboratories, Hercules, Calif.) in TBS buffer (20 mM Tris-HCl, pH 7.5, 14 mM NaCl) for 1 h at room temperature prior to the incubation with polyclonal rabbit anti-HSVtk antibody or monoclonal mouse anti-GRP78 antibody (StressGen, British Columbia, Canada), or monoclonal mouse anti-b-actin antibody (Sigma Chemical Co.) 1 h at room temperature. For all the primary antibodies, 1:1000 dilutions were used. The secondary antibodies used were: goat anti-rabbit IgG conjugated with horseradish peroxidase (Promega, Wis.) and diluted 1:3000 in TBS buffer for detecting HSVTK; and goat anti-mouse IgG conjugated with horseradish peroxidase (Promega, Wis.) and diluted 1:5000 in TBS buffer for detecting GRP78 and β-actin. The immunocomplexes were detected with the Enhanced Chemiluminescence (ECL) kit (Amersham Life Science Inc.).

In Vitro GCV-sensitivity Assay. Individual clones of B/C10ME cells transduced with either the G1TkSvNa or the GlNaGrpTk retroviral vector were seeded in duplicate at $5 \times 10^3$ cells/well in a 6-well plate. On day three after seeding, the cells were incubated with either control medium or 0.1 mg/ml GCV. Fresh GCV was added daily to the cells, which were counted every 3 days using the trypan blue dye exclusion method. For glucose starvation treatment, on the second day after seeding, the cells were maintained on glucose-free DMEM supplemented with dialyzed fetal calf serum for a period of 30 h. After the 30 h, the cells were incubated with 0.1 mg/ml GCV. GCV was added daily while the culture medium was changed every third day for all cell cultures. When the cells reached approximately 70% confluency, the cultures were transferred to 10-cm diameter dishes.

Assay for In Vitro Bystander Effect. To measure the GCV killing effect, non-transduced B/C10ME cells were co-cultured with different ratio of B/C10ME clonal cell lines stably transfected with GlNaGrpTk. Typically, a total of 3000 cells with various ratios (90%:10%; 75%:25%; 50%:50%) were plated in quadruplicate in 96 well plate and treated with 10 mg/ml GCV for 10 days. The number of remaining viable cells was measured by cell proliferation assay (Promega, Wis.).

Tumor Formation. Confluent cultures of B/C10ME clones were harvested with trypsin-EDTA (Gibco/BRL) and washed three times in PBS. Approximately $2 \times 10^7$ viable cells were resuspended in 200 ml of PBS. Six- to eight-week-old BALB/c mice obtained from Jackson Laboratory were subcutaneously injected with an 18-gauge needle in their right flank. Tumors were palpable within 12 days of inoculation and bi-perpendicular measurements were taken of the progressively growing tumor daily. Tumor growth was monitored by measurement of the larger and smaller diameters. At the indicated times post-injection, mice were injected with GCV daily at a dosage of 100 mg/kg of body weight for about 10 days. Tumors were judged to have regressed after losing both measurability and palpability. For each retroviral construct, multiple injections of 2 to 3 independently derived transduced clonal cell lines were performed.

Immunohistochemistry. Tumor tissues were removed, stored at −80° C. and cut by cryostat to 4 mm sections. The frozen sections were fixed by 10% formalin solution for 15 min and treated with 3% hydrogen peroxide. A rabbit polyclonal antibody against HSVtk was added to the sections for 1 h at room temperature. After washing three times with PBS, a HRP labeled polymer conjugated to goat anti-rabbit antibody (Dako, Carpenteria, Calif.) was added and incubated for 30 min. After three washes with PBS, the slides were stained with 3,3-diaminobenzidine (DAB) and counterstained with methylgreen and covered with regular permount and viewed under a Zeiss microscope.

Figure 6A:
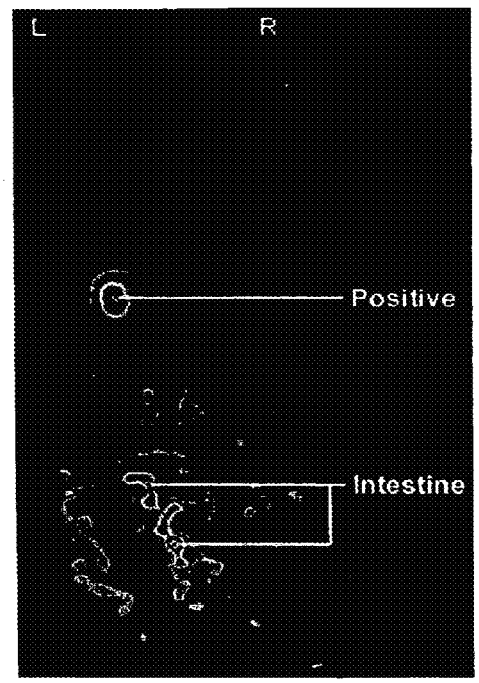
FIG. 6 shows micropet images of hypoxia inducible HSVtk expression in a murine mammary adenocarcinoma model. The mice were bearing tumors derived from a murine mammary adenocarcinoma cell line, TSA, which has been stably transfected with a retroviral vector, G1NaGRP-HSVtk, containing the GRP78 promoter that drives HSVtk gene expression.
Figure 6B:
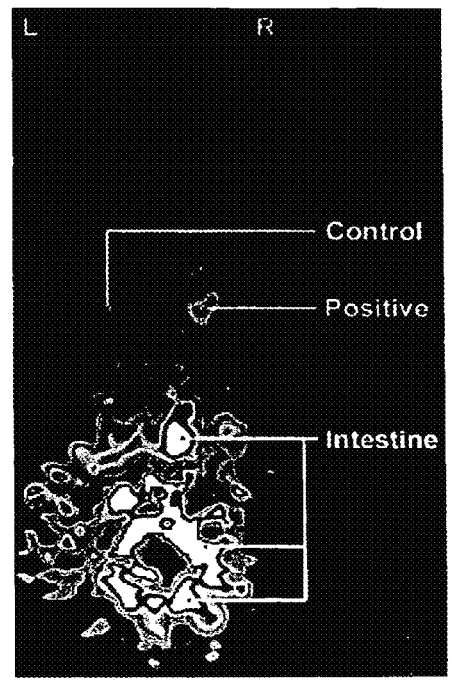

MicroPET Imaging of HSVtk Expression. The hypoxia-inducibility of the GRP78 promoter was demonstrated in vivo by microPET scanning to detect GRP78-driven HSV-tk gene expression, using the isotope-labeled substrate [$^{18}$F] FHBG. Tumors were established by subcutaneous inoculation of TSA murine breast cancer cells that had been stably pre-transduced with a standard replication-defective retrovirus containing the GRP78-driven HSV-tk cassette. These tumors were then examined by microPET scanning in the absence or presence of further hypoxia induction by photodynamic treatment. FIG. 6 shows microPET images of hypoxia inducible HSVtk expression in a murine mammary adenocarcinoma model. The mcroPET scan was performed as described (Gambhir et al. PNAS, 96:2333, 1999). The isotope-labeled substrate was [$^{18}$F]FHBG (Alauddin, Nuclear Medicine & Biology. 25:175, 1998). In Panel A, the grp78 promoter is able to drive high level HSVtk expression in sizable solid tumors. A tumor was formed in the left (L) shoulder area in a BALB/C mouse by injecting s.c. 2×10$^7$ of G1NaGRP-HSVtk transfected TSA cells. The microPET scan was performed when the tumor was about 1.5 cm in diameter. The red color denotes high HSVtk activity. In Panel B, the grp78 promoter is inducible by hypoxia activated by photodynamic treatment (PDT). Two tumors were formed simultaneously on the left (L) and right (R) shoulder areas of a BALB/C mouse the same as described in A. The microPET scan was performed when tumor sizes reached about 0.6 cm in diameter and about 12 hours after the tumor on the right had received PDT which induces hypoxia in vivo. The two tumors were of approximately the same size before PDT treatment and the relatively larger contour seen on the image on the R tumor is due to hemorrhage and edema after PDT treatment.

Production of Transgenic Animals. The present invention further provides a transgenic mouse line expressing the β-galactosidase (lacZ) gene driven by the GRP78 promoter. Significantly, lacZ staining was observed in a variety of tumor tissues that developed in the transgenic mice after exposure to chemical carcinogens, but was not observed in any normal organs. Furthermore, using a plasmid containing the grp78 endoplasmic reticulum stress response element (ERSE) linked to the minimal MMTV promoter, extremely low basal levels and a 25-fold induction by glucose starvation was observed upon transient transfection in the human prostate cancer cell line PC3.

The transgene of the invention was injected into fertilized eggs from superovaluated 4 to 5 week old F1 (C57BL/6J xCBA/J) females impregnated by F1 (C57BL/6J×CBA/J) adult males. Psuedopregant females for embryo transfer were produced by matings between CD1 adult females and vasectomized CD1 adult males.

Mice of about 1.5 to 2 years of age were treated with the chemical carcinogen every week for 6 months. Tumors developed in both transgenic mice as well as non-transgenic controls. Tumors and normal organs were excised and stained for β-galactosidase expression. Blue color indicates that the grp78 promoter was active and driving the expression of the β-gal gene. The results showed no expression in normal organs indicating low grp78 promoter activity in normal tissues but elevated expression in tumorous and/or inflammatory tissues.

Results

Features of Stress-inducible grp78/BiP Promoter. Under glucose starvation and anaerobic conditions, the grp78 promoter is highly induced. The mammalian grp78 promoter is functionally redundant and contains multiple stress-inducible elements interacting with the CBF and YY1 transcription factors (Li et al., J. Biol. Chem., 268:12003, 1993; Roy et al., J. Biol. Chem., 271:28995, 1996; Li et al., Mol. Cell. Biol., 17:54, 1997). The genetic code for endoplasmic reticulum stress signaling leading to grp gene induction consists of two units of a 19 base pair (bp) sequence motif (CCAAT)N9 (CCACG) (SEQ ID NO:1) termed ERSE. This sequence contains a tripartite structure, with a high affinity CBF/NF-Y binding site separated by precisely 9 by of a GC rich sequence motif to a low affinity YY1 binding site.

Figure 1:
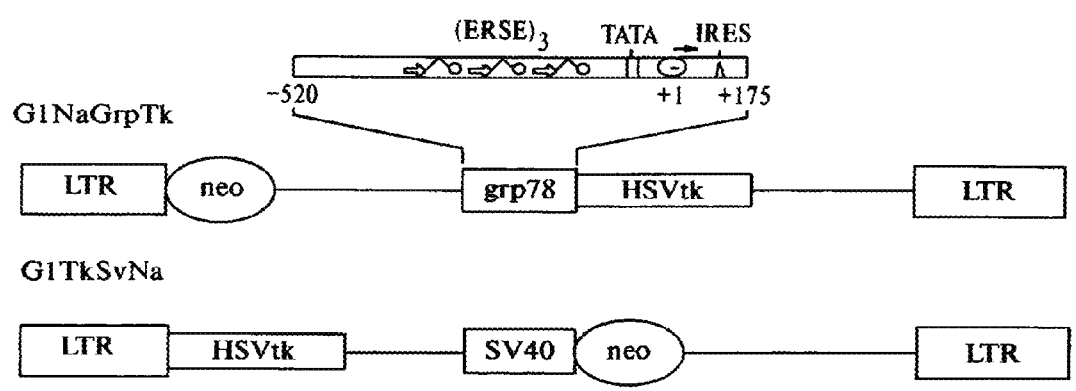
FIG. 1 shows a schematic drawing of the recombinant retroviral vectors. In the GlNaGrpTk vector, the MuLV LTR drives the expression of neomycin phosphotransferase (neo) gene that is used as a selection marker. In this same vector, the grp78 promoter, (spanning nucleotides −520 to +175 of the grp78 gene) drives the HSVtk gene. The grp78 promoter fragment contains three copies of the endoplasmic reticulum stress element (ERSE), the TATA box, and an internal ribosome entry site (IRES) in the 5' untranslated region downstream of its transcription initiation site (+1). In the G1TkSvNa vector, the MuLV LTR drives expression of the HSVtk gene, while the SV40 promoter drives the neo gene.

In the construction of the retroviral vector G1NaGrpTk, the rat grp78 promoter, spanning 520 by upstream and 175 by downstream of the site of initiation of transcription, serves as an internal promoter driving the expression of the HSVtk gene (FIG. 1). This 695 by grp78 promoter subfragment contains three ERSEs, a TATA element and an internal ribosome entry site, a unique and useful feature of the 5' untranslated region of grp78 that allows internal initiation of translation (Macejak et al., Nature, 353:90, 1991). In the G1NaGrpTk vector, the MuLV LTR directs the expression of the neo gene that is used as a selection marker. For comparison, instead of using a retroviral vector with another internal promoter such as SV40 that has previously been shown to be ineffective to drive a reporter gene in a tumor environment (Gazit et al., Cancer Res., 55:1660, 1995), the G1TkSvNa retroviral vector was used. In this vector, the viral LTR drives the expression of the HSVtk gene, while the Simian virus SV40 promoter drives neo expression (FIG. 1). The rationale for choosing G1TkSvNa is that it represents an improved retroviral vector for suicide gene therapy and is the vector of choice in current clinical protocols (Anderson, Nature, 392 (Suppl):25, 1998). Both vectors were transduced into B/C10ME, a murine fibrosarcoma cell line that is syngeneic with the Balb/c mice. The advantage of the B/C10ME as a model system is that it has been previously established that kinetics of tumor growth and subsequent regression can be readily monitored in the recipient mice.

Glucose Deprivation Induces grp78-driven HSVtk Expression in vitro. To create clonal B/C10ME cell lines with stably integrated retroviral vectors, the cells infected with the retroviruses were selected with G418. Serial dilution plating was performed after selection to isolate individual clones. The individual clones were expanded and analyzed. Under standard culture conditions, B/C10ME cells transduced with either retroviral construct exhibited equivalent plating efficiencies and growth rates (see below). Thus, the basic growth properties of the transduced cells in vitro were similar.

Figure 2A:
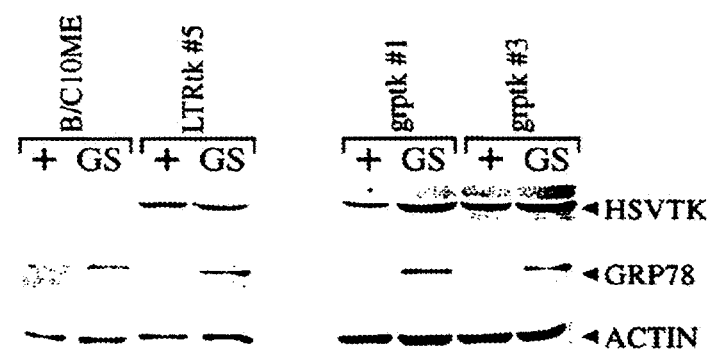
FIG. 2 shows induction of HSVTK by the grp78 promoter under glucose starvation conditions. Panel A shows equal amounts of cell lysates from the parental B/C10ME cells, independently derived clonal cell lines transduced with G1TKSvNa (LTRtk#5), or transduced with GlNaGrpTk (grptk#1 and grptk#3) were subjected to Western blot analysis with antibodies against HSVTK, GRP78 and β-actin. The cells were grown under normal culture medium (+) or glucose-starved (GS) conditions for 24 h. Panel B shows a bar graph indicating the intensity of the protein bands quantitated by densitometry and normalized against that of actin serving as an internal loading control. The relative levels of HSVTK under normal culture or glucose-starved conditions were plotted below the autoradiograms, with the protein level in control cells set as 1.
Figure 2B:
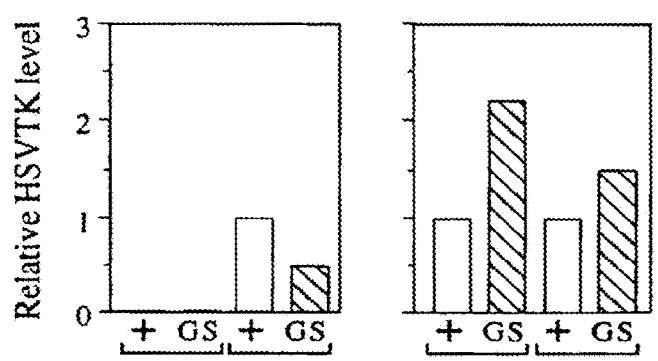

To test for the efficacy of the LTR and the grp78 promoter to drive expression of the HSVTK protein, total cell lysates were prepared from individual clonal lines under normal culture and glucose starved conditions. The proteins were separated by SDS-PAGE and subjected to Western blot analysis. The levels of HSVTK, GRP78 and β-actin in each sample was measured. As expected, there was no detectable HSVTK in the non-transduced B/C10ME cells (FIG. 2). In the clonal line with the HSVtk gene driven by the LTR, there was HSVTK expression under normal culture conditions. However, when the cells were subjected to glucose starvation for 24 h, while the level of GRP78 was induced and the level of HSVTK was reduced. In contrast, in the clonal cell lines with the HSVtk gene driven by the grp78 promoter, the level of HSVTK was upregulated in glucose-starved cells (FIG. 2).

Figure 3A:
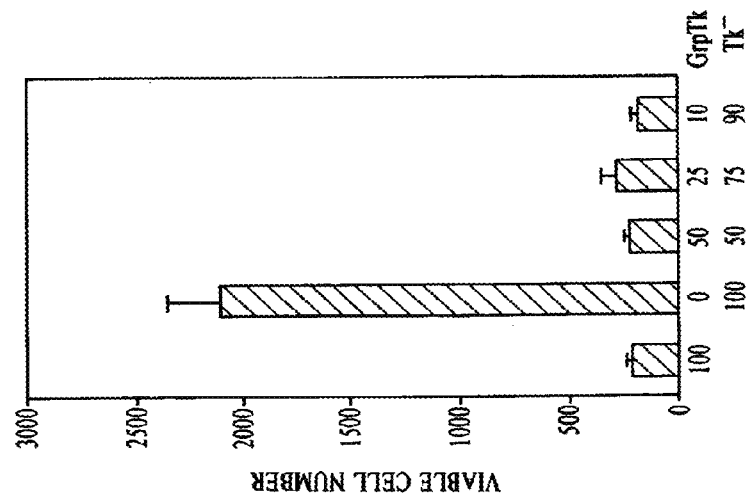
FIG. 3 shows the results of an in vitro GCV-sensitivity assay for B/C10ME cells. Panel A is a line graph showing about $5 \times 10^3$ of G1TkSvNa/clone #3 clones were seeded in duplicate into 6-well plates and incubated without (X) or with 0.1 (closed circles, open circles) μg/ml GCV starting at day 3 as indicated. The cells were then incubated in normal medium (-) or pretreated in glucose-free medium ( - - - ), and the number of surviving cells were determined by the trypan blue exclusion method. Panel B shows data generated by the procedure used in A except that GlNaGrpTk/clone #3 cells were used. Panel C, in vitro bystander effect, non-transduced B/C10ME cells (TK⁻) were co-cultured with different ratio of B/C10ME clonal cell lines stably transfected with GlNaGrpTk. A total of 3,000 cells with various ratios were plated in quadruplicate in 96 well plate and treated with 10 mg/ml GCV for 10 days. The number of remaining viable cells was measured by cell proliferation assay.
Figure 3B:
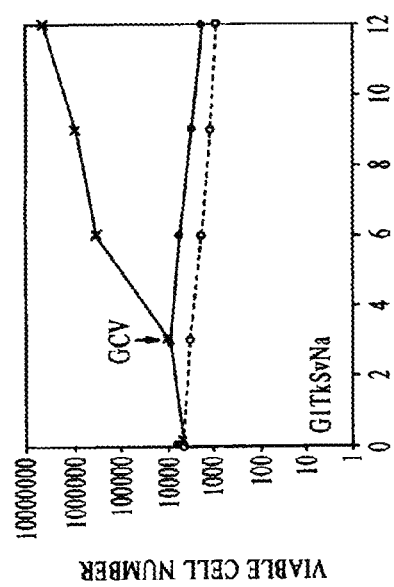
Figure 3C:
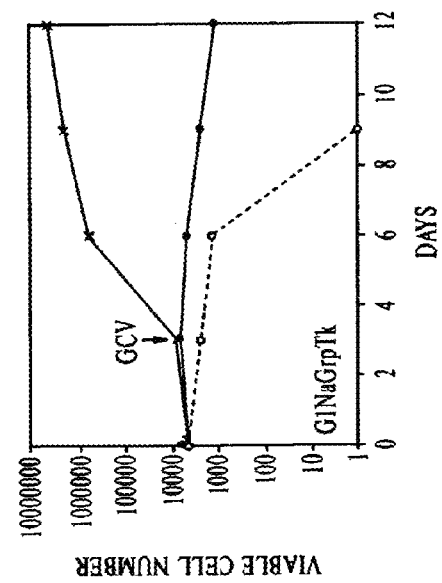

To analyze HSVtk activity under normal and glucose-starved conditions, clonal cell lines derived from B/C10ME transduced cells with each respective retroviral construct were analyzed using an in vitro GCV-sensitivity assay (FIG. 3). For this purpose, about 5,000 cells were seeded in duplicates in 6-well plates, and on the third day of seeding, either remained untreated, or incubated with 0.1 µg/ml of GCV. One set of cells was cultured in normal culture medium containing 4.5 mg/ml of glucose, and an identical set of cells was maintained in glucose-free medium supplemented with dialyzed fetal calf serum for 30 h prior to the addition of GCV. Example of the GCV survival test for a typical B/C10ME derived clone transduced with G1TkSvNa (G1TkSvNa/clone #3) is shown in FIG. 3, Panel A. Without the addition of GCV the cells continued to grow exponentially, and by the end of the 12th day, the cell number had reached $4 \times 10^6$. Addition of GCV resulted in loss of live cells at a similar rate for both sets of cells. By the end of the 12th day, about 1,000 cells survived (FIG. 3, Panel A). Thus, for the LTR-driven HSVtk, the sensitivity to GCV was similar in cells cultured in normal or glucose-free medium.

The results of the GCV survival assay for a typical clonal line (G1NaGrpTk/clone #3) derived from B/C10ME cells transduced with GlNaGrpTk is shown in FIG. 3, Panel B. Under normal culture conditions, the growth rate as well as sensitivity to GCV was similar to that driven by the LTR. However, in contrast to the LTR-driven HSVtk cells, when GlNaGrpTk transduced cells were pretreated with the glucose-free medium, decrease in viable cells was much more pronounced. Thus by day 9 there were no more surviving cells. Further, to demonstrate these cells exhibit a bystander effect, HSVTK-positive cells were co-cultured with various ratios of non-transduced HSVTK-negative cells. Over 90% killing was observed when only 10% of GlNaGrpTk cells are present in the culture (FIG. 3, Panel C). Collectively, these in vitro studies show that the retroviral construct containing an internal grp78 promoter produces higher levels of HSVtk inducible by glucose deprivation, thereby enhancing the sensitivity of tumor cells to GCV.

Figure 4A:
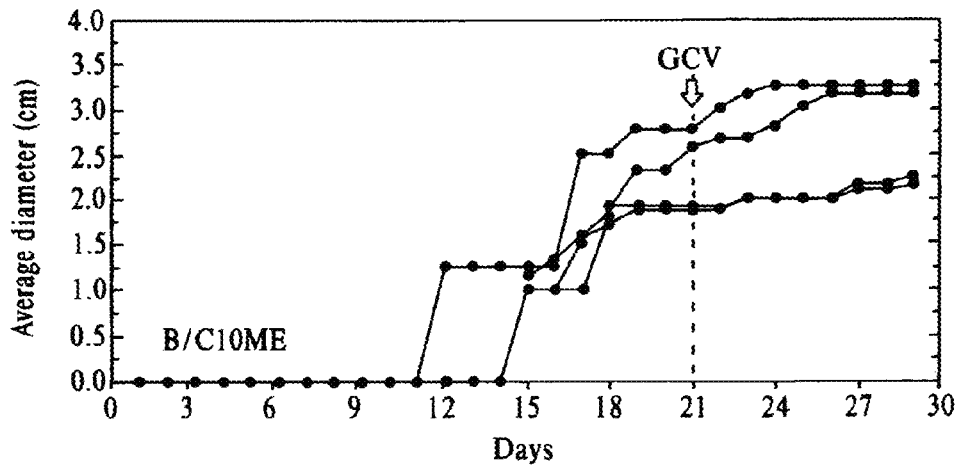
FIG. 4 shows tumor growth curves for B/C10ME fibrosarcoma. Panel A shows B/C10ME cells, B, three independently derived G1TkSvNa clonal derivatives (#2, #3, #5) or C, two independently derived GlNaGrpTk clonal derivatives (#1, #3) were used. Equivalent numbers of $2 \times 10^7$ viable cells were subcutaneously injected into BALB/c mice. Bi-perpendicular measurements were taken over a period of 29 days. GCV (as indicated by arrows) was administered daily starting at day 21 at a dosage of 100 mg/kg of body weight.
Figure 4B:
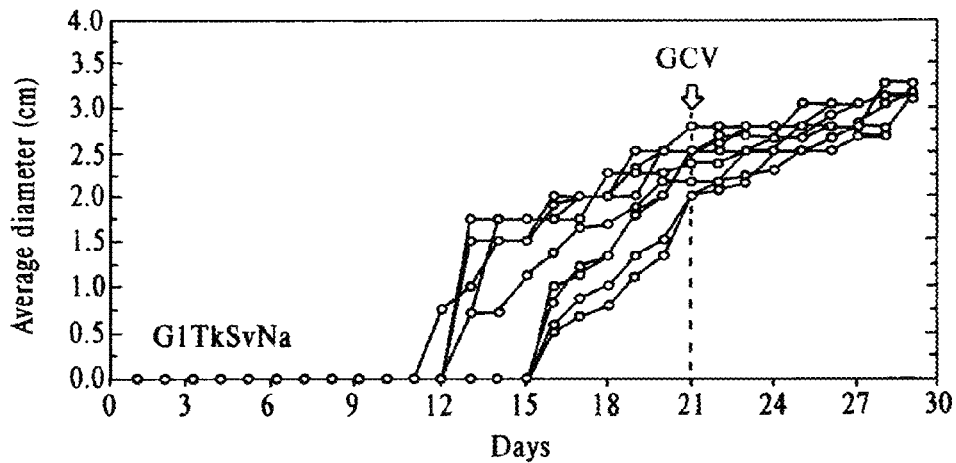
Figure 4C:
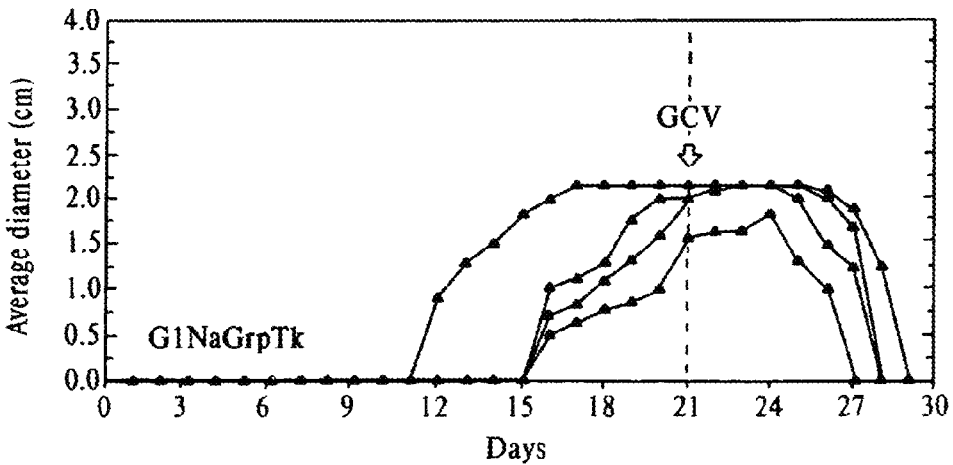

Complete Eradication of Tumors in G1NaGrpTk Transduced Cells. To directly compare the therapeutic efficacy of the G1NaGrpTk vector with G1TkSvNa, B/C10ME clones transduced with the respective retroviral constructs were injected subcutaneously at a dose of $2 \times 10^7$ cells per BALB/c mouse. As controls, the parental, non-transduced cells were also injected. Tumors were palpable after 12 days of injection. At day 21, when the average tumor diameter reached about 2 cm, GCV was administered. The rationale for starting the GCV treatment when the tumor had reached a sizable mass instead of just being palpable is that this will offer a more vigorous test for the potency of the retroviral vectors. For the parental B/C10ME cells, upon addition of GCV, the tumors continued to grow at various rates and growth was arrested as tumors reached substantial mass (FIG. 4, Panel A). In the nine mice injected with three different G1TkSvNa clonal cell lines, the majority of tumor growth was arrested upon GCV treatment for two to three days but subsequently, tumor growth continued (FIG. 4, Panel B). Thus, at this stage of tumor growth, the LTR-driven HSVtk was insufficient to mediate efficient GCV toxicity. In contrast, in mice injected with the G1NaGrpTk clonal cell lines containing the internal grp78 promoter driving HSVtk expression, tumor regression was observed in all four mice injected with two independently derived clonal lines following GCV treatment. By day 29, there were no visible tumors in any of the animals (FIG. 4, Panel C). Complete tumor eradication was also observed in mouse mammary tumor clonal cell lines transduced with G1NaGrpTk. All mice remained healthy and developed no tumors after withdrawal of the GCV treatment.

Figure 5A:
FIG. 5 shows immunohistochemistry staining of HSVtk protein expression in B/C10ME tumor tissues from mice. Panel A shows that, after counterstaining the tissue section with methyl green, no DAB stain can be detected in tumor from non-transduced B/C10ME cells; B, isolated patches of HSVtk protein expression can be observed by cytoplasmic brown DAB staining in tumor from B/C10ME cells transduced with G1TkSvNa; and C, high level of HSVtk protein expression as shown by dark cytoplasmic brown DAB staining in tumor from B/C10ME cells transduced with GlNaGrpTk. The magnification is 200×.
Figure 5B:
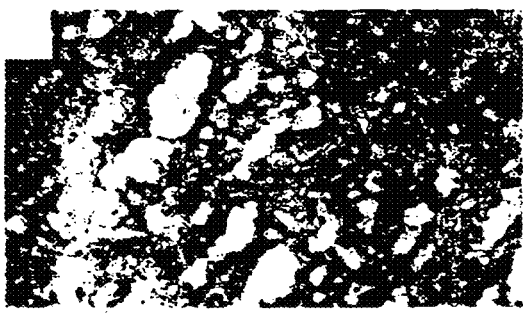
Figure 5C:
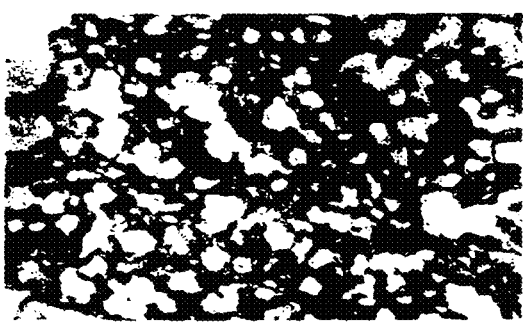

To confirm that higher efficacy of G1NaGrpTk is due to higher expression of HSVTK within the tumor, immunohistochemistry-staining for the HSVTK protein was performed with the tumor tissues. Examples of the immunohistochemistry-staining using antibody against HSVTK in B/C10ME tumors are shown in FIG. 5. The parental cells showed the absence of HSVTK protein staining (FIG. 5, Panel A). A much higher level of staining was detected in tumors derived from G1NaGrpTk transduced cells (FIG. 5, Panel C) as compared to that derived from G1TkSvNa (FIG. 5, Panel B). Notably, the HSVTK staining for the G1TkSvNa was in isolated patches, suggesting there were areas within the tumor unfavorable for LTR-driven gene expression. In contrast, the staining for G1NaGrpTk was much more enhanced across the tumor section as previously observed with the endogenous grp78 transcript and the neo mRNA driven by the grp78 promoter. Thus, within the tumor environment, G1NaGrpTk containing an internal stress-inducible grp78 promoter is more effective in directing high level HSVTK expression than the retroviral LTR.

In cancer gene therapy, a major technical difficulty is the lack of specificity in targeting suicide gene expression in the anatomic site of tumors. The present invention provides a novel approach to this problem by using a stress-inducible promoter from the grp78 gene to direct the expression of the HSVtk gene in solid tumors. Increased grp78 protein expression is detected in chemical- and radiation-transformed cells, as well as in tumor cells that become drug-resistant. Within the tumor environment, glucose deprivation, chronic anoxia, and acidic pH induce the GRPs, in particular grp78. Thus, grp78 mRNA levels are elevated in a variety of tumors, correlating with tumor size. These results indicate that in regions of the tumors deprived of glucose and oxygen, the cells experience a stress response resulting in the specific activation of the grp78 promoter.

The present invention provides a truncated rat grp78 promoter with most of the distal basal elements removed while retaining its array of stress-inducible elements (FIG. 1). When used as an internal promoter in a retroviral construct, the truncated rat grp78 promoter can drive increased expression of HSVTK in vitro under glucose-starved conditions (FIGS. 2 and 3). These in vitro studies confirm that the internal grp78 promoter is capable of inducing a high level of marker gene transcript in glucose-deprived cells, in contrast to the HaMSV LTR that was repressed. In vivo, the G1NaGrpTk retroviral vector was highly effective in directing HSVTK expression within the tumor environment (FIG. 5), leading to complete eradication of sizable tumors in their syngeneic host after GCV treatment. The potency of G1NaGrpTk, coupled with the known bystander effects of suicide gene approach, suggests that this type of vector could offer distinct advantages in solid tumor cancer therapy.

In addition, the present study shows that mice with regressed tumors remained tumor free after withdrawal of GCV treatment. These data indicate that protective immunity might have been induced in such mice, preventing regrowth of tumors. In support, there are several examples of long-lasting antitumor immunity in various tumor models in response to HSVtk transduction and GCV treatments. For example, the immune response elicited by mammary adenocarcinoma cells transduced with interferon-γ and suicide genes may induce regression of lung metastases (Nanni et al., Hum. Gene Ther., 9:217, 1998). These data indicate that tumors transduced with suicide genes can be used as live anti-tumor vaccines (Santodonato et al., Gene Ther., 4:1246-, 1997). In support of the this, it has recently been discovered that induction of apoptosis in tumor cells leads to a dramatic change in antigen presentation which could lead to enhancement of the cell mediated immune response to the tumor.

Transgenic animals containing a nucleic acid construct of the invention were produced and used to identify biologically stressed tissue in the animal. FIG. 7 shows the presence of the LacZ transgene in transgenic mice. Panel A is a diagram of the grp78/LacZ Transgene construct comprising about 3000 base pairs of the grp78 regulatory sequence operably linked to the LacZ gene. Panel B, upper gel, shows a Southern hybridization resulting in the identification of a LacZ nucleic acid sequence in transgenic animals (Tg 132-147) containing the construct shown in Panel A. In the lower gel, a grp78 cDNA probe that hybridizes to the grp78 gene was used to demonstrate that similar amounts of total DNA were loaded in to each lane of the gel. The transgenic sequences were identified using a suitably labeled LacZ probe. Non-transgenic (Non-Tg) animals do not contain the LacZ sequence. Panel C is a bar graph showing the LacZ activity present in hamster cells transfected with a plasmid containing a nucleic acid construct shown in panel A (grp78/LacZ) or a plasmid expressing LacZ from the SV40 large T antigen promoter sequence (SV40/LacZ). Cells were treated with the calcium ionophore A23187 to induce biological stress. Untreated and treated activity is indicated.

Carcinogen treatment of wild-type (+/+), heterozygous for the grp78/LacZ transgene (Tg/+) or homozygous for the grp78/LacZ transgene (Tg/Tg). The carcinogen (7,12-dimethyl benz[a]anthracene) was applied subcutaneously on a weekly basis over a period of six months. Subsequently, normal and tumorous tissue were isolated and stained for detection of LacZ expression (FIG. 8).

Color photographs of normal (non-neoplastic) tissue derived from transgenic mice that are homozygous for the grp78/LacZ transgene (Tg/Tg) or tissue derived from wild-type (non-transgenic) mice (+/+) are sown in FIG. 9. The mice, and tissue derived therefrom, were treated as described in FIG. 8.

Color photographs of tumorous tissues removed from mice treated as described in FIG. 8 are shown in FIG. 10. Tissue from mice heterozygous for the grp78/LacZ transgene (Tg/+), homozygous for the grp78/LacZ transgene (Tg/Tg) and wild-type (+/+) are indicated. Note that, following LacZ-specific histological staining, LacZ expression is indicated in tumorous tissue derived from Tg/+ mice as well as tissue derived from Tg/Tg mice.

Additionally, photographs of tumorous tissues removed from mice treated as described in FIG. 8 are shown in FIG. 11. Tissue from mice heterozygous for the grp78/LacZ transgene (Tg/+) or homozygous for the grp78/LacZ transgene (Tg/Tg) are indicated. Note that, following LacZ-specific histological staining, LacZ expression is indicated in tumorous tissue derived from Tg/+ mice as well as tissue derived from Tg/Tg mice.

A number of embodiments of the invention have been described. Nevertheless, it will be understood that various modifications may be made without departing from the spirit and scope of the invention. Accordingly, other embodiments are within the scope of the following claims.

What is claimed is:

1. A method for inhibiting cell proliferation associated with glucose starvation comprising:
    a) transducing a target cell capable of cell proliferation with a recombinant retroviral vector comprising a nucleic acid construct, the nucleic acid construct comprising (i) at least one glucose responsive protein 78 (grp78) non-coding regulatory sequence that comprises a sequence from about 520 base pairs 5' of the site of initiation of transcription of the rat grp78 coding sequence to about 175 base pairs 3' of the site of initiation of transcription of the rat grp78 coding sequence; and (ii) a heterologous nucleic acid sequence operatively linked to the regulatory sequence, wherein the heterologous sequence comprises a structural gene that encodes a biologically active enzyme that converts a non-therapeutically effective compound to a therapeutically-effective compound in vivo;
    b) activating the glucose responsive protein 78 (grp78) non-coding regulatory sequence such that the heterologous nucleic acid sequence comprising a structural gene that encodes a biologically active protein is expressed; and
    c) contacting the cell with a non-therapeutically effective compound that is subsequently converted to a therapeutically-effective compound by the biologically active protein,
    wherein the therapeutically effective compound inhibits cell proliferation associated with glucose starvation.

2. The method of claim 1, wherein the subject is a mammal.
3. The method of claim 2, wherein the mammal is a mouse.
4. The method of claim 2, wherein the mammal is a human.
5. The method of claims 1, wherein the administration is by in vivo administration.
6. The method of claim 5, wherein the in vivo administration is by direct administration.
7. The method of claim 1, wherein the cell proliferative disorder is a neoplastic disorder.
8. The method of claim 7, wherein the neoplastic disorder is selected from the group consisting of lung cancer, colon-rectum cancer, breast cancer, prostate cancer, urinary tract cancer, uterine cancer lymphoma, oral cancer, pancreatic cancer, leukemia, melanoma, stomach cancer, thyroid cancer, liver cancer, and brain cancer and ovarian cancer.

* * * * *